US008756079B2

(12) United States Patent
Yegnanarayanan

(10) Patent No.: US 8,756,079 B2
(45) Date of Patent: *Jun. 17, 2014

(54) METHODS AND APPARATUS FOR APPLYING USER CORRECTIONS TO MEDICAL FACT EXTRACTION

(75) Inventor: Girija Yegnanarayanan, Raleigh, NC (US)

(73) Assignee: Nuance Communications, Inc., Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/492,276

(22) Filed: Jun. 8, 2012

(65) Prior Publication Data

US 2012/0245961 A1  Sep. 27, 2012

Related U.S. Application Data

(63) Continuation of application No. 13/030,959, filed on Feb. 18, 2011.

(51) Int. Cl.
*G06Q 50/22* (2012.01)
*G06Q 50/24* (2012.01)

(52) U.S. Cl.
USPC .................................. 705/3; 705/2

(58) Field of Classification Search
USPC ........................................ 705/2, 3
See application file for complete search history.

(56) References Cited

U.S. PATENT DOCUMENTS

| 4,477,698 | A | 10/1984 | Szlam et al. |
| 4,965,763 | A | 10/1990 | Zamora |
| 5,146,439 | A | 9/1992 | Jachmann et al. |
| 5,253,164 | A | 10/1993 | Holloway et al. |
| 5,325,293 | A | 6/1994 | Dorne |
| 5,327,341 | A | 7/1994 | Whalen et al. |
| 5,392,209 | A | 2/1995 | Eason et al. |
| 5,519,808 | A | 5/1996 | Benton, Jr. et al. |
| 5,544,360 | A | 8/1996 | Lewak et al. |

(Continued)

FOREIGN PATENT DOCUMENTS

WO  WO 2010/117424 A2  10/2010

OTHER PUBLICATIONS

M*Modal, Two-Minute Guide to M*Modal, 1 page.

(Continued)

*Primary Examiner* — Neal Sereboff
*Assistant Examiner* — Maroun Kanaan
(74) *Attorney, Agent, or Firm* — Wolf, Greenfield & Sacks, P.C.

(57) ABSTRACT

A method for applying a user correction to medical fact extraction may include extracting, using at least one processor, a first set of one or more medical facts from a first portion of a text documenting a patient encounter. A correction to the first set of medical facts may be received from a user documenting the patient encounter. A second set of one or more medical facts may be extracted from a second portion of the text based at least in part on the user's correction to the first set of medical facts. An apparatus for applying a user correction to medical fact extraction may include at least one processor and at least one computer-readable storage medium storing processor-executable instructions that, when executed by the at least one processor, perform the above-described method. At least one computer-readable storage medium may be encoded with computer-executable instructions that perform the above-described method.

9 Claims, 12 Drawing Sheets

(56) References Cited

U.S. PATENT DOCUMENTS

| | | |
|---|---|---|
| 5,602,982 A | 2/1997 | Judd et al. |
| 5,664,109 A | 9/1997 | Johnson et al. |
| 5,675,788 A | 10/1997 | Husick et al. |
| 5,748,888 A | 5/1998 | Angelo et al. |
| 5,799,268 A | 8/1998 | Boguraev |
| 5,809,476 A | 9/1998 | Ryan |
| 5,812,882 A | 9/1998 | Raji et al. |
| 5,832,450 A | 11/1998 | Myers et al. |
| 5,857,212 A | 1/1999 | Van De Vanter |
| 5,875,448 A | 2/1999 | Boys et al. |
| 5,893,109 A | 4/1999 | DeRose et al. |
| 5,970,463 A | 10/1999 | Cave et al. |
| 5,974,412 A | 10/1999 | Hazlehurst et al. |
| 6,006,221 A | 12/1999 | Liddy et al. |
| 6,014,663 A | 1/2000 | Rivette et al. |
| 6,021,202 A | 2/2000 | Anderson et al. |
| 6,052,693 A | 4/2000 | Smith et al. |
| 6,055,494 A | 4/2000 | Friedman |
| 6,088,437 A | 7/2000 | Amick |
| 6,182,029 B1 | 1/2001 | Friedman |
| 6,192,112 B1 | 2/2001 | Rapaport et al. |
| 6,289,353 B1 | 9/2001 | Hazlehurst et al. |
| 6,292,771 B1 | 9/2001 | Haug et al. |
| 6,347,329 B1 | 2/2002 | Evans |
| 6,360,215 B1 | 3/2002 | Judd et al. |
| 6,374,225 B1 | 4/2002 | Hejna, Jr. |
| 6,405,165 B1 | 6/2002 | Blum et al. |
| 6,415,256 B1 | 7/2002 | Ditzik |
| 6,434,547 B1 | 8/2002 | Mishelevich et al. |
| 6,438,533 B1 | 8/2002 | Spackman et al. |
| 6,438,545 B1 | 8/2002 | Beauregard et al. |
| 6,553,385 B2 | 4/2003 | Johnson et al. |
| 6,854,086 B2 | 2/2005 | Umen et al. |
| 6,865,258 B1 | 3/2005 | Polcyn |
| 6,915,254 B1 | 7/2005 | Heinze et al. |
| 6,925,436 B1 | 8/2005 | Franz et al. |
| 6,947,936 B1 | 9/2005 | Suermondt et al. |
| 6,950,994 B2 | 9/2005 | Dharap |
| 6,961,699 B1 | 11/2005 | Kahn et al. |
| 6,996,445 B1 | 2/2006 | Kamijo |
| 7,016,844 B2 | 3/2006 | Othmer et al. |
| 7,124,144 B2 | 10/2006 | Christianson et al. |
| 7,233,938 B2 | 6/2007 | Carus et al. |
| 7,236,932 B1 | 6/2007 | Grajski |
| 7,299,110 B2 | 11/2007 | Gupta et al. |
| 7,315,811 B2 | 1/2008 | Cote et al. |
| 7,379,946 B2 | 5/2008 | Carus et al. |
| 7,493,253 B1 | 2/2009 | Ceusters et al. |
| 7,542,909 B2 | 6/2009 | Cote et al. |
| 7,610,192 B1 * | 10/2009 | Jamieson .......................... 704/9 |
| 7,860,717 B2 | 12/2010 | Uhrbach et al. |
| 7,996,223 B2 | 8/2011 | Frankel et al. |
| 8,024,176 B2 | 9/2011 | Carus et al. |
| 8,095,544 B2 | 1/2012 | Boone et al. |
| 8,185,553 B2 | 5/2012 | Carus et al. |
| 2002/0007285 A1 | 1/2002 | Rappaport |
| 2002/0095313 A1 | 7/2002 | Haq |
| 2002/0128861 A1 | 9/2002 | Lau et al. |
| 2002/0143824 A1 | 10/2002 | Lee et al. |
| 2002/0169764 A1 | 11/2002 | Kincaid et al. |
| 2003/0046080 A1 | 3/2003 | Hejna, Jr. |
| 2003/0046264 A1 | 3/2003 | Kauffman |
| 2003/0061201 A1 | 3/2003 | Grefenstette et al. |
| 2003/0067495 A1 | 4/2003 | Pu et al. |
| 2003/0079186 A1 | 4/2003 | Gondo et al. |
| 2003/0115080 A1 | 6/2003 | Kasravi et al. |
| 2003/0208382 A1 | 11/2003 | Westfall |
| 2003/0233345 A1 | 12/2003 | Perisic et al. |
| 2004/0103075 A1 | 5/2004 | Kim et al. |
| 2004/0139400 A1 | 7/2004 | Allam et al. |
| 2004/0186746 A1 | 9/2004 | Angst et al. |
| 2004/0186747 A1 | 9/2004 | Nakano et al. |
| 2004/0205638 A1 | 10/2004 | Thomas et al. |
| 2004/0220895 A1 | 11/2004 | Carus et al. |
| 2004/0243545 A1 | 12/2004 | Boone et al. |
| 2004/0243551 A1 | 12/2004 | Boone et al. |
| 2004/0243552 A1 | 12/2004 | Titemore |
| 2004/0243614 A1 | 12/2004 | Boone et al. |
| 2005/0108010 A1 | 5/2005 | Frankel et al. |
| 2005/0114122 A1 | 5/2005 | Uhrbach et al. |
| 2005/0120020 A1 | 6/2005 | Carus et al. |
| 2005/0120300 A1 | 6/2005 | Schwager et al. |
| 2005/0144184 A1 | 6/2005 | Carus et al. |
| 2005/0149747 A1 | 7/2005 | Wesinger, Jr. et al. |
| 2005/0165598 A1 | 7/2005 | Cote et al. |
| 2005/0192792 A1 | 9/2005 | Carus et al. |
| 2005/0192793 A1 | 9/2005 | Cote et al. |
| 2006/0206943 A1 | 9/2006 | Ellison et al. |
| 2006/0253895 A1 | 11/2006 | Brandofino et al. |
| 2006/0272025 A1 | 11/2006 | Mononen |
| 2007/0143857 A1 | 6/2007 | Ansari |
| 2007/0283444 A1 | 12/2007 | Jang |
| 2007/0294745 A1 | 12/2007 | Tan et al. |
| 2007/0300287 A1 | 12/2007 | Wynne et al. |
| 2008/0228769 A1 * | 9/2008 | Lita et al. .......................... 707/6 |
| 2009/0192822 A1 | 7/2009 | Regulapati et al. |
| 2010/0114597 A1 * | 5/2010 | Shreiber et al. .................. 705/2 |
| 2010/0250236 A1 | 9/2010 | Jagannathan et al. |
| 2010/0324927 A1 * | 12/2010 | Tinsley ............................ 705/2 |
| 2012/0166225 A1 * | 6/2012 | Albro et al. ...................... 705/3 |
| 2012/0215551 A1 | 8/2012 | Flanagan et al. |
| 2012/0215557 A1 | 8/2012 | Flanagan et al. |
| 2012/0215558 A1 | 8/2012 | Flanagan et al. |
| 2012/0215559 A1 | 8/2012 | Flanagan et al. |
| 2013/0035961 A1 | 2/2013 | Yegnanarayanan |

OTHER PUBLICATIONS

Batty et al., "The development of a portable real-time display of voice source characteristics", IEEE, 2:419-422 (2000).

Song et al., "A Graphical Interface to a Semantic Medical Information System", Journal of Foundations of Computing and Decision Sciences, 22(2), 1997.

Song et al., "A Cognitive Model for the Implementation of Medical Problem Lists, Proceedings of the First Congress on Computational Medicine", Public Health and Biotechnology, Austin, Texas, 1994.

Song et al., A Graphical Interface to a Semantic Medical Information System, Karp-95 Proceedings of the Second International Symposium on Knowledge Acquisition, Representation and Processing, pp. 107-109, 1995.

Epic Web Training Manual, pp. 1-33, 2002.

Hieb, Research Note, NLP Basics for Healthcare, Aug. 16, 2002.

Shalizi et al., "Pattern Discovery in Time Series, Part 1: Theory, Algorithm, Analysis and Convergence", Journal of Medicine Leaning Research? (2002) ?-? Submitted Oct. 28, 2002; Published ?/2002.

Nevill-Manning et al., "The Development of Holte's 1R Classifier", Department of Computer Science.

Cutting et al., A Practical Part-of-Speech, Xerox Palo Alto Research Center.

Zavrel et al., Recent Advances in Memory-Based Part-of-Speech Tagging, ILK/Computational Linguistics.

Brill, Some Advances in Transformation-Based Part-of-Speech Tagging, Spoken Language Systems Group.

Nivre, DAC723: Language Technology Finite State Morphology, Vaxjo University of Mathematics and Systems Engineering, p. 1-11.

Creutz, "Morphology and Finite-State Transducers", Oct. 31, 2001, Chapter 3, Jurafsky & Martin.

Http // www comp lancs ac uk/computing/research/stemming/general/index htm, printed Jul. 19, 2004.

http // www comp lancs ac uk/computing/research/stemming/general/stemmingerrors htm, printed Jul. 19, 2004.

http // www comp lancs ac uk/computing/research/stemming/general/performance htm, printed Jul. 19, 2004.

Lee et al., "Cleansing Data for Mining and Warehousing, Lecture Notes in Computer Science", vol. 1677 archive, Proceedings of the 10th International Conference on Database and Expert Systems Applications, pp. 751-760, Springer-Verlag, London, 1999.

Van Rijsbergen, Information Retrieval, 2nd Ed., Ch. 5, Butterworths, London, 1979.

(56) References Cited

OTHER PUBLICATIONS

Day, Extracting Knowledge from Text Using Learning by Constraint Relaxation (LCR), CSI, www csi-inc com/CSI/pdf/jday icim02 pdf.

Gale et al., "Discrimination Decisions for 100,000-Dimensional Spaces", Current Issues in Computational Linguistics, Kluwer Academic Publishers, pp. 429-450.

Daelemans, et al., TIMBL: Tiburg Memory Based Learner, Version 5,0, Reference Guide, ILK Research Group Technical Report Series No. 04-02 (ILK-0402), ILK Research Group, Tilbur University, Tilburg, Netherlands, 2004.

Case Study: Massachusetts Medical Society, http // www Microsoft com/resources/casesstudies/CaseStudyasp?caseStudyID=14931, posted Jan. 13, 2004.

Braithwaite, Continuity of Care Record (CCR), http // www hl7 org/library/himss/2004Orlando/ContnuityofCareRecord pdf.

Wagemann, EHR vs. CCR: What is the Difference Between the Electronic Health Record and the Continuity of Care Record?, Medical Records Institute, 2004.

Press Release: Kryptiq Announces Support of CCR Initiative and Introduces New Solutions that Enable Information Portability, Accessibility and Clinical System Interoperability, http // www kryptiq com/News/PressRelease/27 html, posted Feb. 2004.

Work Item Summary: WK4363 Standard Specification for the Continuity of Care Record (CCR), http // www astm org/cqi-bin/SoftCart exe/Database.Cart/Workitems/WK4363htm?+mystore, Mar. 3, 2004.

Continuity of Care Record (CCR): The Concept Paper of the CCR v. 2.1b, http // www bhtinfo com/CCR Concept%20Paper. 1.5doc.

Continuity of Care Record, American Academy of Family Physicians, http // www aafp org/x24962.xml?printxml, posted Nov. 12, 2003.

Continuity of Care Record (CCR), AAFP Center for Health Information Technology, http // www centerforhit or /x201.xml, posted Aug. 20, 2004.

Core Measures Web Page, Joint Commission on Accreditation of Healthcare Organizations, http // www icaho org/pms/core+measures, printed Mar. 22, 2004.

Specifications Manual for National Implementation of Hospital Core Measures, v. 2.0, Joint Commission on Accreditation of Healthcare Organizations, http // www icaho or/pms/core+measures/information+on+final+specifications htm.

Code Information and Education Web Page, American Medical Association, http // www amassn org/ama/pub/category/3884 html, printed Mar. 22, 2004.

Category III CPT Codes, American Medical Association, http // www ama-assn org/ama/pub/article/3885-4897 html, printed Mar. 22, 2004.

ICD-9-CM Preface (FY04), http // ftp cdc gove/pub/health statistics/ NCHS/publications/ICD9-cm/2004/prefac05 rtf.

ICD-9-CM Official Guidelines for Coding and Reporting, effective Oct. 1, 2003.

Yang et al., "Faster Algorithm of String Comparison", Pattern Analysis and Applications, vol. 6, No. 1, Apr. 2003, pp. 122-133.

"Hardware Reference Manual", Release 3 for DOS, Revised Jan. 1994, PIKA Technologies, Inc., Ontario, Canada, available at, http // www pikatechnologies com/downloads/legacy/Ava%20B-Series%20Hardware%20Manual pdf, (last accessed Jul. 25, 2005).

Customizing D/41 Call Analysis:, date unknown, Intel Corp., Santa Clara, California, available at http // resource intel com/telecom/support/appnotes/custd41d htm, (last accessed Jul. 25, 2005).

International Search Report for PCT Application Serial No. PCT/US2004/016878, International Filing Date May 28, 2004.

Smith et al., "Microarras: An Advanced Full-Text Retrieval and Analysis System", ACM 1987, p. 187-195.

* cited by examiner

FIG. 2

Patient Name [John Doe] Sex [M] Creation Date [01-18-2011]
Document Type [Discharge Summary]

Chief complaint: Patient is presenting chest pain and shortness of breath.

Medical history: The patient is hypertensive. He is also obese.

Social history: He smokes one pack per day. Drinks occasionally.

⊟ Problems(:)
| Name | Status |

Add Fact

⊟ Medications(0)
| Name | Status | Schedules |

Add Fact

⊟ Allergies(0)
| Name | Type | Status | Substance | Reactions |

Add Fact

⊟ Social History (:)

Add Alcohol Fact | Add Tobacco Fact

[Process] [Cancel]

Patient Name John Doe  Sex M  Creation Date 01-18-2011
Document Type Discharge Summary — 300

Problems  Medications  Allergies  Social History  Procedures  Vital Signs    Hide All Chief complaint: Patient is presenting chest pain and shortness of breath. — 315

Medical history: The patient is hypertensive. He is also obese. — 313, 319, 317

Social history: He smokes one pack per day. Drinks occasionally.

— 210, 200, 220

⊟ Problems(4) — 310

Add Fact

| | Name | Status |
|---|---|---|
| x | Unspecified Chest Pain — 314, 312 | active |
| x | Shortness of Breath | active |
| x | Unspecified Essential Hypertension — 318, 316 | history |
| x | Obesity Unspecified | history |

⊟ Medications(1) — 320

Add Fact

| | Name | Status | Schedules |
|---|---|---|---|
| x | | | None |

⊟ Allergies(0) — 330

Add Fact

| | Name | Type | Status |
|---|---|---|---|

— 230

Save | Dictate | Complete | Cancel

METHODS AND APPARATUS FOR APPLYING USER CORRECTIONS TO MEDICAL FACT EXTRACTION

RELATED APPLICATIONS

This application is a continuation of U.S. patent application Ser. No. 13/030,959, filed Feb. 18, 2011, entitled "METHODS AND APPARATUS FOR FORMATTING TEXT FOR CLINICAL FACT EXTRACTION," which is incorporated herein by reference in its entirety.

BACKGROUND OF INVENTION

1. Field of Invention

The techniques described herein are directed generally to the field of clinical documentation, and more particularly to techniques for the creation and use of patient records in clinical settings.

2. Description of the Related Art

Clinical documentation is an important process in the healthcare industry. Most healthcare institutions maintain a longitudinal medical record (e.g., spanning multiple observations or treatments over time) for each of their patients, documenting the patient's history, encounters with clinical staff within the institution, treatment received, and plans for future treatment. Such documentation facilitates maintaining continuity of care for the patient across multiple encounters with various clinicians over time. In addition, when an institution's medical records for large numbers of patients are considered in the aggregate, the information contained therein can be useful for educating clinicians as to treatment efficacy and best practices, for internal auditing within the institution, for quality assurance, etc.

Historically, each patient's medical record was maintained as a physical paper folder, often referred to as a "medical chart", or "chart". Each patient's chart would include a stack of paper reports, such as intake forms, history and immunization records, laboratory results and clinicians' notes. Following an encounter with the patient, such as an office visit, a hospital round or a surgical procedure, the clinician conducting the encounter would provide a narrative note about the encounter to be included in the patient's chart. Such a note could include, for example, a description of the reason(s) for the patient encounter, an account of any vital signs, test results and/or other clinical data collected during the encounter, one or more diagnoses determined by the clinician from the encounter, and a description of a plan for further treatment. Often, the clinician would verbally dictate the note into an audio recording device or a telephone giving access to such a recording device, to spare the clinician the time it would take to prepare the note in written form. Later, a medical transcriptionist would listen to the audio recording and transcribe it into a text document, which would be inserted on a piece of paper into the patient's chart for later reference.

Currently, many healthcare institutions are transitioning or have transitioned from paper documentation to electronic medical record systems, in which patients' longitudinal medical information is stored in a data repository in electronic form. Besides the significant physical space savings afforded by the replacement of paper record-keeping with electronic storage methods, the use of electronic medical records also provides beneficial time savings and other opportunities to clinicians and other healthcare personnel. For example, when updating a patient's electronic medical record to reflect a current patient encounter, a clinician need only document the new information obtained from the encounter, and need not spend time entering unchanged information such as the patient's age, gender, medical history, etc. Electronic medical records can also be shared, accessed and updated by multiple different personnel from local and remote locations through suitable user interfaces and network connections, eliminating the need to retrieve and deliver paper files from a crowded file room.

SUMMARY OF INVENTION

One embodiment is directed to a method comprising: receiving an original text that is a representation of a narration of a patient encounter provided by a clinician; re-formatting the original text, using at least one processor, to produce a formatted text; extracting one or more clinical facts from the formatted text, wherein a first fact of the one or more clinical facts is extracted from a first portion of the formatted text, wherein the first portion of the formatted text is a formatted version of a first portion of the original text; and maintaining a linkage between the first fact and the first portion of the original text.

Another embodiment is directed to apparatus comprising at least one processor, and a memory storing processor-executable instructions that, when executed by the at least one processor, perform a method comprising: receiving an original text that is a representation of a narration of a patient encounter provided by a clinician; re-formatting the original text to produce a formatted text; extracting one or more clinical facts from the formatted text, wherein a first fact of the one or more clinical facts is extracted from a first portion of the formatted text, wherein the first portion of the formatted text is a formatted version of a first portion of the original text; and maintaining a linkage between the first fact and the first portion of the original text.

Another embodiment is directed to at least one computer-readable storage medium encoded with a plurality of computer-executable instructions that, when executed, perform a method comprising: receiving an original text that is a representation of a narration of a patient encounter provided by a clinician; re-formatting the original text to produce a formatted text; extracting one or more clinical facts from the formatted text, wherein a first fact of the one or more clinical facts is extracted from a first portion of the formatted text, wherein the first portion of the formatted text is a formatted version of a first portion of the original text; and maintaining a linkage between the first fact and the first portion of the original text.

Another embodiment is directed to a method comprising: extracting, using at least one processor, a plurality of clinical facts from a free-form narration of a patient encounter provided by a clinician, wherein the plurality of clinical facts comprises a first fact and a second fact, wherein the first fact is extracted from a first portion of the free-form narration, and wherein the second fact is extracted from a second portion of the free-form narration; and providing to a user a first indicator that indicates a first linkage between the first fact and the first portion of the free-form narration, and a second indicator, different from the first indicator, that indicates a second linkage between the second fact and the second portion of the free-form narration.

Another embodiment is directed to apparatus comprising at least one processor, and a memory storing processor-executable instructions that, when executed by the at least one processor, perform a method comprising: extracting a plurality of clinical facts from a free-form narration of a patient encounter provided by a clinician, wherein the plurality of clinical facts comprises a first fact and a second fact, wherein the first fact is extracted from a first portion of the free-form narration, and wherein the second fact is extracted from a second portion of the free-form narration; and providing to a user a first indicator that indicates a first linkage between the first fact and the first portion of the free-form narration, and a second indicator, different from the first indicator, that indicates a second linkage between the second fact and the second portion of the free-form narration.

Another embodiment is directed to at least one computer-readable storage medium encoded with a plurality of computer-executable instructions that, when executed, perform a method comprising: extracting a plurality of clinical facts from a free-form narration of a patient encounter provided by a clinician, wherein the plurality of clinical facts comprises a first fact and a second fact, wherein the first fact is extracted from a first portion of the free-form narration, and wherein the second fact is extracted from a second portion of the free-form narration; and providing to a user a first indicator that indicates a first linkage between the first fact and the first portion of the free-form narration, and a second indicator, different from the first indicator, that indicates a second linkage between the second fact and the second portion of the free-form narration.

Another embodiment is directed to a method comprising: collecting a set of one or more clinical facts from a clinician's encounter with a patient; determining from the set of facts, using at least one processor, that an additional fact that provides additional specificity to the set of facts may possibly be ascertained from the patient encounter; and alerting a user that the additional fact may possibly be ascertained from the patient encounter.

Another embodiment is directed to apparatus comprising at least one processor, and a memory storing processor-executable instructions that, when executed by the at least one processor, perform a method comprising: collecting a set of one or more clinical facts from a clinician's encounter with a patient; determining from the set of facts that an additional fact that provides additional specificity to the set of facts may possibly be ascertained from the patient encounter; and alerting a user that the additional fact may possibly be ascertained from the patient encounter.

Another embodiment is directed to at least one computer-readable storage medium encoded with a plurality of computer-executable instructions that, when executed, perform a method comprising: collecting a set of one or more clinical facts from a clinician's encounter with a patient; determining from the set of facts that an additional fact that provides additional specificity to the set of facts may possibly be ascertained from the patient encounter; and alerting a user that the additional fact may possibly be ascertained from the patient encounter.

Another embodiment is directed to a method comprising: collecting a set of one or more clinical facts from a clinician's encounter with a patient; determining, using at least one processor, that an unspecified diagnosis not included in the set of facts may possibly be ascertained from the patient encounter; and alerting a user that the unspecified diagnosis may possibly be ascertained from the patient encounter.

Another embodiment is directed to apparatus comprising at least one processor, and a memory storing processor-executable instructions that, when executed by the at least one processor, perform a method comprising: collecting a set of one or more clinical facts from a clinician's encounter with a patient; determining that an unspecified diagnosis not included in the set of facts may possibly be ascertained from the patient encounter; and alerting a user that the unspecified diagnosis may possibly be ascertained from the patient encounter.

Another embodiment is directed to at least one computer-readable storage medium encoded with a plurality of computer-executable instructions that, when executed, perform a method comprising: collecting a set of one or more clinical facts from a clinician's encounter with a patient; determining that an unspecified diagnosis not included in the set of facts may possibly be ascertained from the patient encounter; and alerting a user that the unspecified diagnosis may possibly be ascertained from the patient encounter.

Another embodiment is directed to a method comprising: determining, based on a free-form narration of a patient encounter provided by a clinician, that one or more clinical facts could possibly be ascertained from the patient encounter; providing to a user one or more options corresponding to the one or more clinical facts; receiving from the user a selection of a first option of the one or more options, the first option corresponding to a first fact of the one or more clinical facts; and updating a textual representation of the free-form narration, using at least one processor, to identify the first fact as having been ascertained from the patient encounter.

Another embodiment is directed to apparatus comprising at least one processor, and a memory storing processor-executable instructions that, when executed by the at least one processor, perform a method comprising: determining, based on a free-form narration of a patient encounter provided by a clinician, that one or more clinical facts could possibly be ascertained from the patient encounter; providing to a user one or more options corresponding to the one or more clinical facts; receiving from the user a selection of a first option of the one or more options, the first option corresponding to a first fact of the one or more clinical facts; and updating a textual representation of the free-form narration to identify the first fact as having been ascertained from the patient encounter.

Another embodiment is directed to at least one computer-readable storage medium encoded with a plurality of computer-executable instructions that, when executed, perform a method comprising: determining, based on a free-form narration of a patient encounter provided by a clinician, that one or more clinical facts could possibly be ascertained from the patient encounter; providing to a user one or more options corresponding to the one or more clinical facts; receiving from the user a selection of a first option of the one or more options, the first option corresponding to a first fact of the one or more clinical facts; and updating a textual representation of the free-form narration to identify the first fact as having been ascertained from the patient encounter.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 2 is a screenshot illustrating an exemplary graphical user interface for a clinical fact review system in accordance with some embodiments of the present invention;

FIGS. 3A and 3B are screenshots illustrating an exemplary display of clinical facts in a user interface in accordance with some embodiments of the present invention;

FIG. 4 is a screenshot illustrating an exemplary display of linkage between text and a clinical fact in accordance with some embodiments of the present invention;

FIG. 5 is a screenshot illustrating an exemplary interface for entering a clinical fact in accordance with some embodiments of the present invention;

DETAILED DESCRIPTION

Figure 1:
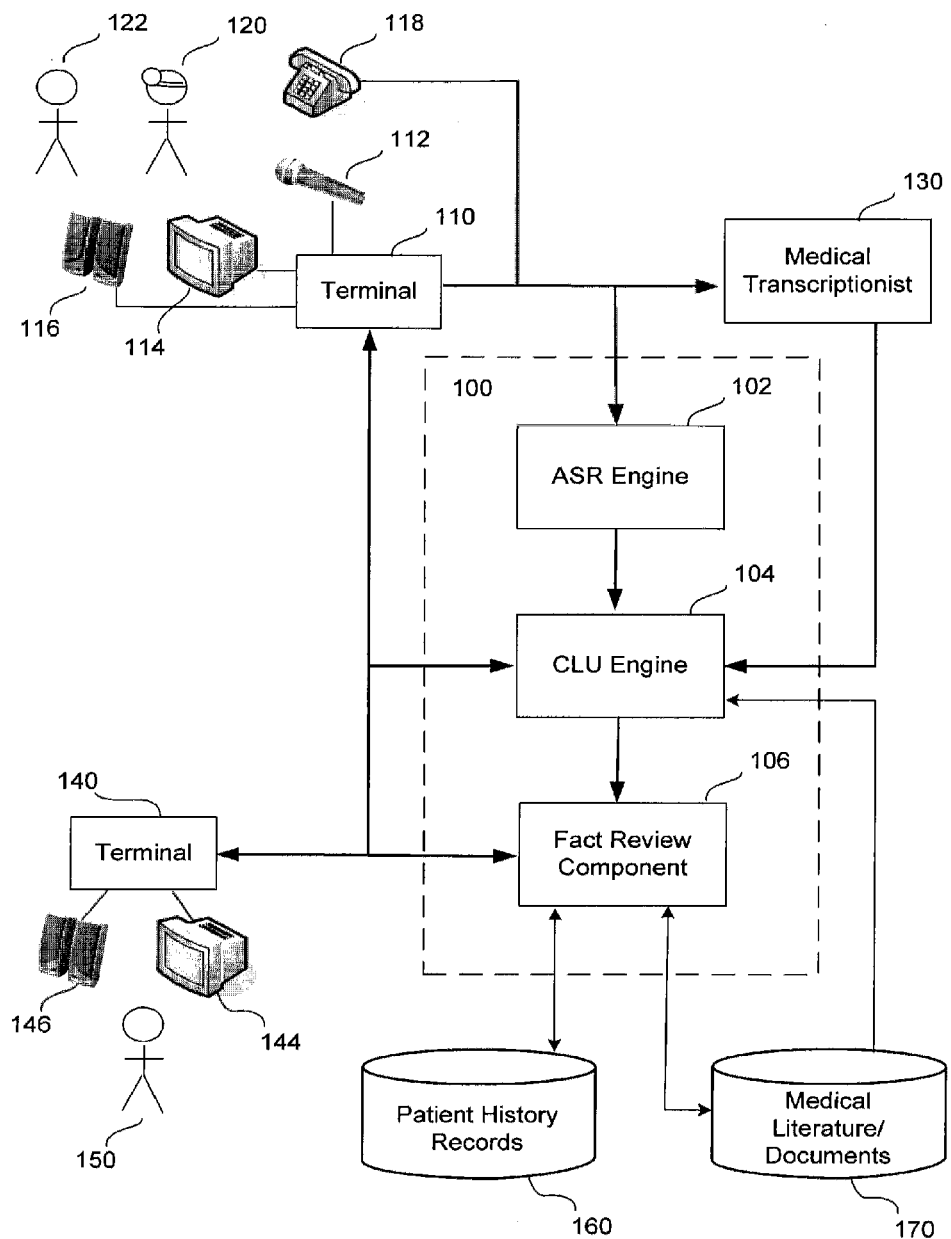
FIG. 1 is a block diagram of an exemplary operating environment for a system in accordance with some embodiments of the present invention.

An Electronic Health Record (EHR) is an electronic medical record that generally is maintained by a specific healthcare institution and contains data documenting the care that a specific patient has received from that institution over time. Typically, an EHR is maintained as a structured data representation, such as a database with structured fields. Each piece of information stored in such an EHR is typically represented as a discrete (e.g., separate) data item occupying a field of the EHR database. For example, a 55-year old male patient named John Doe may have an EHR database record with "John Doe" stored in the patient_name field, "55" stored in the patient_age field, and "Male" stored in the patient_gender field. Data items or fields in such an EHR are structured in the sense that only a certain limited set of valid inputs is allowed for each field. For example, the patient_name field may require an alphabetic string as input, and may have a maximum length limit; the patient_age field may require a string of three numerals, and the leading numeral may have to be "0" or "1"; the patient_gender field may only allow one of two inputs, "Male" and "Female"; a patient_birth_date field may require input in a "MM/DD/YYYY" format; etc.

Typical EHRs are also structured in terms of the vocabulary they use, as clinical terms are normalized to a standard set of terms utilized by the institution maintaining the EHR. The standard set of terms may be specific to the institution, or may be a more widely used standard. For example, a clinician dictating or writing a free-form note may use any of a number of different terms for the condition of a patient currently suffering from an interruption of blood supply to the heart, including "heart attack", "acute myocardial infarction", "acute MI" and "AMI". To facilitate interoperability of EHR data between various departments and users in the institution, and/or to allow identical conditions to be identified as such across patient records for data analysis, a typical EHR may use only one standardized term to represent each individual clinical concept. For example, "acute myocardial infarction" may be the standard term stored in the EHR for every case of a heart attack occurring at the time of a clinical encounter. Some EHRs may represent clinical terms in a data format corresponding to a coding standard, such as the International Classification of Disease (ICD) standard. For example, "acute myocardial infarction" may be represented in an EHR as "ICD-9 410", where 410 is the code number for "acute myocardial infarction" according to the ninth edition of the ICD standard.

To allow clinicians and other healthcare personnel to enter clinical documentation data directly into an EHR in its discrete structured data format, many EHRs are accessed through user interfaces that make extensive use of point-and-click input methods. While some data items, such as the patient's name, may require input in (structured) textual or numeric form, many data items can be input simply through the use of a mouse or other pointing input device (e.g., a touch screen) to make selections from pre-set options in drop-down menus and/or sets of checkboxes and/or radio buttons or the like.

The inventors have recognized, however, that while some clinicians may appreciate the ability to directly enter structured data into an EHR through a point-and-click interface, many clinicians may prefer being unconstrained in what they can say and in what terms they can use in a free-form note, and many may be reluctant to take the time to learn where all the boxes and buttons are and what they all mean in an EHR user interface. In addition, many clinicians may prefer to take advantage of the time savings that can be gained by providing notes through verbal dictation, as speech can often be a faster form of data communication than typing or clicking through forms.

Accordingly, some embodiments described herein relate to techniques for enhancing the creation and use of structured electronic medical records, using techniques that enable a clinician to provide input and observations via a free-form narrative clinician's note. Some embodiments involve the automatic extraction of discrete clinical facts, such as could be stored as discrete structured data items in an electronic medical record, from a clinician's free-form narration of a patient encounter. In this manner, free-form input may be provided, but the advantages of storage, maintenance and accessing of clinical documentation data in electronic forms may be maintained. For example, the storage of a patient's clinical documentation data as a collection of discrete structured data items may provide the benefits of being able to query for individual data items of interest, and being able to assemble arbitrary subsets of the patient's data items into new reports, orders, invoices, etc., in an automated and efficient manner.

Automatic extraction of clinical facts from a free-form narration may be performed in any suitable way using any suitable technique(s), as aspects of the present invention are not limited in this respect. In some embodiments, pre-processing may be performed on a free-form narration prior to performing fact extraction, to determine the sequence of words represented by the free-form narration. Such pre-processing may also be performed in any suitable way using any suitable technique(s), as aspects of the present invention are not limited in this respect. For example, in some embodiments, the clinician may provide the free-form narration directly in textual form (e.g., using a keyboard or other text entry device), and the textual free-form narration may be automatically parsed to determine its sequence of words. In other embodiments, the clinician may provide the free-form narration in audio form as a spoken dictation, and an audio recording of the clinician's spoken dictation may be received and/or stored. The audio input may be processed in any suitable way prior to or in the process of performing fact extraction, as aspects of the invention are not limited in this respect. In some embodiments, the audio input may be processed to form a textual representation, and fact extraction may be performed on the textual representation. Such processing to produce a textual representation may be performed in any suitable way. For example, in some embodiments, the audio recording may be transcribed by a human transcriptionist, while in other embodiments, automatic speech recognition (ASR) may be performed on the audio recording to obtain a textual representation of the free-form narration provided via the clinician's dictation. Any suitable automatic speech recognition technique may be used, as aspects of the present invention are not limited in this respect. In other embodiments, speech-to-text conversion of the clinician's audio dictation may not be required, as a technique that does not involve processing the audio to produce a textual representation may be used to determine what was spoken. In one example, the sequence of words that was spoken may be determined directly from the audio recording, e.g., by comparing the audio recording to stored waveform templates to determine the sequence of words. In other examples, the clinician's speech may not be recognized as words, but may be recognized in another form such as a sequence or collection of abstract concepts. It should be appreciated that the words and/or concepts represented in the clinician's free-form narration may be represented and/or stored as data in any suitable form, including forms other than a textual representation, as aspects of the present invention are not limited in this respect.

In some embodiments, one or more clinical facts may be automatically extracted from the free-form narration (in audio or textual form) or from a pre-processed data representation of the free-form narration using a clinical language understanding (CLU) engine. Such a CLU engine may be implemented in any suitable form, as aspects of the present invention are not limited in this respect. In some embodiments, a CLU engine may be implemented using techniques such as those described in U.S. Pat. No. 7,493,253, entitled "Conceptual World Representation Natural Language Understanding System and Method", which is incorporated herein by reference in its entirety. Such a CLU engine may make use of a formal ontology linked to a lexicon of clinical terms. The formal ontology may be implemented as a relational database, or in any other suitable form, and may represent semantic concepts relevant to the clinical domain, as well as linguistic concepts related to ways the semantic concepts may be expressed in natural language.

In some embodiments, concepts in a formal ontology used by a CLU engine may be linked to a lexicon of clinical terms and/or codes, such that each clinical term and each code is linked to at least one concept in the formal ontology. In some embodiments, the lexicon may include the standard clinical terms and/or codes used by the institution in which the CLU engine is applied. For example, the standard clinical terms and/or codes used by an EHR maintained by the institution may be included in the lexicon linked to the CLU engine's formal ontology. In some embodiments, the lexicon may also include additional clinical terms used by the various clinicians within the institution when providing their free-form narrations. Such additional clinical terms may be linked, along with their corresponding standard clinical terms, to the appropriate shared concepts within the formal ontology. For example, the standard term "acute myocardial infarction" as well as other corresponding terms such as "heart attack", "acute MI" and "AMI" may all be linked to the same abstract concept in the formal ontology—a concept representing an interruption of blood supply to the heart. Such linkage of multiple clinical terms to the same abstract concept in some embodiments may relieve the clinician of the burden of ensuring that only standard clinical terms preferred by the institution appear in the free-form narration. For example, in some embodiments, a clinician may be free to use the abbreviation "AMI" or the colloquial "heart attack" in his free-form narration, and the shared concept linkage may allow the CLU engine to nevertheless automatically extract a fact corresponding to "acute myocardial infarction".

In some embodiments, a formal ontology used by a CLU engine may also represent various types of relationships between the concepts represented. One type of relationship between two concepts may be a parent-child relationship, in which the child concept is a more specific version of the parent concept. In some embodiments, any other type(s) of relationship useful to the process of clinical documentation may also be represented in the formal ontology. For example, one type of relationship may be a symptom relationship. In one example of a symptom relationship, a concept linked to the term "chest pain" may have a relationship of "is-symptom-of" to the concept linked to the term "heart attack". Other types of relationships may include complication relationships, comorbidity relationships, interaction relationships (e.g., among medications), and many others. Any number and type(s) of concept relationships may be included in such a formal ontology, as aspects of the present invention are not limited in this respect.

In some embodiments, automatic extraction of clinical facts from a clinician's free-form narration may involve parsing the free-form narration to identify clinical terms that are represented in the lexicon of the CLU engine. Concepts in the formal ontology linked to the clinical terms that appear in the free-form narration may then be identified, and concept relationships in the formal ontology may be traced to identify further relevant concepts. Through these relationships, as well as the linguistic knowledge represented in the formal ontology, one or more clinical facts may be extracted. For example, if the free-form narration includes the clinical term "hypertension" and the linguistic context relates to the patient's past, the CLU engine may automatically extract a fact indicating that the patient has a history of hypertension. On the other hand, if the free-form narration includes the clinical term "hypertension" in a sentence about the patient's mother, the CLU engine may automatically extract a fact indicating that the patient has a family history of hypertension. In some embodiments, relationships between concepts in the formal ontology may also allow the CLU engine to automatically extract facts containing clinical terms that were not explicitly included in the free-form narration. For example, the clinical term "meningitis" can also be described as inflammation in the brain. If the free-form narration includes the terms "inflammation" and "brain" in proximity to each other, then relationships in the formal ontology between concepts linked to the terms "inflammation", "brain" and "meningitis" may allow the CLU engine to automatically extract a fact corresponding to "meningitis", despite the fact that the term "meningitis" was not stated in the free-form narration.

It should be appreciated that the foregoing descriptions are provided by way of example only, and that any suitable technique(s) for extracting a set of one or more clinical facts from a free-form narration may be used, as aspects of the present invention are not limited to any particular fact extraction technique.

The inventors have recognized and appreciated that the automatic extraction of clinical facts directly from a free-form narration of a patient encounter provided by a clinician may create the opportunity for numerous enhancements to processes involved in clinical documentation in healthcare institutions. Some such enhancements may help make it possible for a clinician to efficiently oversee a process involving deriving any one or combination of updated patient records, billing information, ordering information, quality of care assurances, decision support, etc., directly from a free-form narration in a single interactive session with a clinical fact review system.

In some embodiments, automatic extraction of clinical facts from a textual representation of a clinician's free-form narration (e.g., from a text narrative) of a patient encounter may be enhanced by re-formatting the text narrative to facilitate the automatic extraction of the clinical facts. For example, in some embodiments a CLU engine that performs the automatic fact extraction may make use of linguistic knowledge that has some dependency on accurate placement of sentence boundaries in the text narrative. Accordingly, in some embodiments, the fact extraction may be enhanced by adding, removing and/or correcting sentence boundaries in the text narrative to comply with the linguistic structure expected by the CLU engine. Examples of ways in which sentence boundary pre-processing can be implemented are described below. In another example, automatic fact extraction may be enhanced by normalizing section headings in the text narrative to comply with standard section headings used by the healthcare institution for which the clinical documentation is being performed.

In some embodiments, a linkage may be maintained between each extracted clinical fact and the portion of the free-form narration from which that fact was extracted. For example, if a fact corresponding to "acute myocardial infarction" is extracted from a free-form narration because it included the term "heart attack", a linkage may be maintained between that extracted fact and the words "heart attack" in the free-form narration. In some embodiments, while the clinician or another user is reviewing the extracted clinical facts via a user interface to a fact review system, the system may provide one or more indicators to the user (who may be the clinician himself or a different person) of the different linkages between the different extracted facts and the portions of the free-form narration from which they were extracted. Such indicators may be visual indicators, audio indicators, or any other suitable type of indicators, as aspects of the present invention are not limited in this respect. In some embodiments, such linkage indicators may enhance the ability of the clinician or other user to review the extracted facts for accuracy, with reference to the specific parts of the free-form narration that generated them. In some embodiments, if a textual representation of the free-form narration has been re-formatted prior to fact extraction, linkages may still be maintained between the extracted facts and the original text narrative, to allow the user to relate the extracted facts to the narration as it was originally given by the clinician. While some embodiments provide linkage information for each extracted fact, it should be appreciated that aspects of the invention relating to providing linkage information are not so limited, as linkage information may be provided for one or any subset of the extracted facts.

In some embodiments, automatically extracted clinical facts may also be automatically reviewed, and automatic alerts may be provided to the clinician or other user if opportunities are identified for the clinical documentation of the patient encounter to be improved. Such alerts may be visual alerts, audio alerts, or any other suitable type of alerts, as aspects of the present invention are not limited in this respect. In some embodiments, such alerts may be provided to the clinician or other user at a time subsequent to the completion of the patient encounter, and may provide the opportunity for the clinician or other user to provide additional information that was ascertained from the patient encounter but was not originally specified in the free-form narration. In other embodiments, such alerts may be provided to the clinician while the patient encounter is still in progress, and may provide the opportunity for the clinician to initiate further interaction with the patient to ascertain additional information to include in the clinical documentation.

In some embodiments, a fact review system may be programmed with a set of deterministic rules to trigger alerts. For example, a set of deterministic rules may specify that certain extracted facts, certain combinations of extracted facts, certain combinations of extracted facts and terms in the free-form narration, and/or certain combinations of facts extracted from the current patient encounter and facts from the patient's previous history automatically trigger alerts to the user. In other embodiments, the fact review system may be programmed to undertake a probabilistic analysis or apply a statistical model to determine whether information specified in the free-form narration will trigger alerts to the user. It should be appreciated, however, that a fact review system in accordance with embodiments described herein is not limited to any particular programming technique, as any suitable such technique may be used. In addition, it should be appreciated that automatic alerts may also be provided in embodiments that do not involve automatic extraction of clinical facts from a free-form narration. For example, such alerts may also be triggered by clinical facts received as discrete structured data items, such as direct input to an electronic medical record such as an EHR. It should thus be appreciated that alerts may be provided based on analysis of clinical facts collected in any suitable way, as aspects of the present invention are not limited in this respect.

In some embodiments, an alert may be provided when a set of one or more clinical facts is collected from a patient encounter, and it is determined that there is an opportunity to increase the specificity of the set of facts. In some embodiments, it may be determined that an additional fact may possibly be ascertained from the patient encounter, and that the additional fact would add specificity to the set of clinical facts already collected from the patient encounter. In one example, such an additional fact may be a more specific version of one of the original facts, and the specificity of the set of facts may be increased by replacing the original fact with its more specific version, provided that it can truly be ascertained from the patient encounter. For instance, the original fact may describe a condition, and the more specific version may describe the same condition as "acute" or "chronic". In another example, two or more of the original facts, when appearing in combination, may imply an additional fact, and documenting the additional fact may increase the specificity of the record of the patient encounter. In some embodiments, an alert may query the user as to whether an additional fact should actually be ascertained from the patient encounter, and may allow the user to increase the specificity of the facts by documenting the additional fact.

In some embodiments, an alert may be provided when a set of one or more clinical facts is collected from a patient encounter, and it is determined that a diagnosis that was not specified in the set of facts may possibly be ascertained from the patient encounter. In one example, such an unspecified diagnosis may be a known comorbidity of a diagnosis that was included in the set of facts. In another example, the unspecified diagnosis may be a known complication of a procedure or diagnosis included in the set of facts. In yet another example, the unspecified diagnosis may be an identification of the fact that a diagnosis included in the set of facts is actually a complication of a procedure or other diagnosis included in the set of facts, or of a procedure or other diagnosis included in facts from the patient's history prior to the current encounter. Similarly, the unspecified diagnosis may be an identification of the fact that a diagnosis included in facts from the patient's previous history is a complication of a diagnosis ascertained during the current patient encounter. In some embodiments, when the possibility or likelihood of such an unspecified diagnosis is determined from the original set of facts collected from the patient encounter, an alert may query the user (e.g., the clinician or another user) as to whether the unspecified diagnosis should be ascertained from the patient encounter.

In some embodiments, an alert may be provided when a set of one or more clinical facts is collected from a patient encounter, and it is determined that two or more of the facts in the set conflict with each other in some way, or it is determined that one or more of the facts in the set conflict with one or more facts in the patient's history. In some embodiments, a fact review system may be programmed to automatically generate such alerts based on a known set of combinations of facts that have undesirable interactions. For example, an alert may be generated when the set of facts indicate that the patient has been prescribed a certain medication (drug A) in addition to a certain other medication (drug B) with which it negatively interacts, such that the two medications should not be prescribed together. In some embodiments, the prescriptions of both drug A and drug B may be specified in the set of facts collected from the current patient encounter, while in other embodiments, the prescription of drug A may be specified in a fact from the current patient encounter, and the prescription of drug B may be specified in a fact contained in a record of the patient's history with the institution. Thus, in some embodiments, the fact review system may access both facts collected from a current patient encounter and facts from the patient's historical records to determine whether alerts should be generated. In some embodiments, an alert to a conflict may be triggered by a combination of facts, at least one of which does not correspond to a medication. For example, alerts may be provided for contraindications related to a combination of a medication with an allergy, a medication with a diagnosis, a medication with a patient's age or gender, a medication with a condition indicated in the patient's history, a medical procedure with any of the foregoing characteristics, or any other combination of a planned treatment with another clinical fact from the current patient encounter or from the patient's history for which the planned treatment is known to be contraindicated.

In some embodiments, an alert may be provided when a set of one or more clinical facts is collected from a patient encounter, and it is determined that there is an opportunity to add to the clinical documentation of the patient encounter for quality review purposes. In some embodiments, a fact review system may be programmed with a set of deterministic rules to generate automatic alerts in response to certain facts or certain combinations of facts, based on a standard set of quality of care measures. Such a quality of care standard may be proprietary and unique to the specific healthcare institution or may be a standard that is not institution specific, such as that of the Physician Quality Reporting Initiative (PQRI) or that of the Joint Commission on Accreditation of Healthcare Organizations (JCAHO). Any suitable quality of care standard may be used, as aspects of the present invention are not limited to any particular quality of care standard. In some embodiments, when a collected fact or combination of facts is associated with a certain recommended action on the part of the clinician according to the quality of care standard, an alert may be provided to query the user as to whether the recommended action was performed.

In some embodiments, a mechanism may be provided to adaptively filter the automatic alerts generated by the fact review system, by learning from the clinician's or other user's interaction with the system over time. For example, if it is determined that a particular user consistently ignores a particular type of alert, the system may stop issuing similar alerts when they are triggered by future facts. In some embodiments, the adaptive learning may be specific to each individual user and may help to prevent alert fatigue, which may involve frustration at repeatedly being bothered by an alert that the user does not find relevant. In some embodiments, the adaptive learning may involve the collection of data regarding patterns of facts that tend to be present when the user ignores alerts, and the system may filter out future alerts that match those patterns of facts. In some embodiments, adaptive alert filtering may be performed based on rules or statistical usage patterns on an institutional level, such that alerts not considered relevant for the specific healthcare institution in which the fact review system is operating are not provided.

In some embodiments, a human user other than the clinician may review the set of clinical facts collected from a patient encounter, and may manually (e.g., not automatically, but involving human action) cause one or more alerts to be issued to the clinician that were not issued automatically by the fact review system. Such a human user may manually cause alerts to be issued in any suitable way, as aspects of the invention are not limited in this respect. In one example, the human user may provide instructional input to the fact review system to cause the fact review system to generate an alert specified by the human user. In other examples, the human user may use a different method and/or system, other than the fact review system, to issue an alert to the clinician. Such a different method in some embodiments need not be machine-based, as aspects of the invention are not limited in this respect. In some embodiments, the human user may have access to the patient's past medical history within and/or external to the healthcare institution, for example in the form of an electronic medical record and/or past clinical documents relating to the patient's care at the institution and/or elsewhere. In some embodiments, the human user may make reference to this past medical history, in addition to the clinical facts from the current patient encounter, to determine whether to manually cause an alert to be issued to the clinician. In some embodiments, the human user may determine to issue an alert, similar to any of the various types of automatic alerts described above, if the facts and the patient's history indicate a situation in which the automatic fact review system should have generated an automatic alert, but it failed to accurately recognized the situation. In some embodiments, if the clinician chose to ignore an alert automatically generated by the fact review system, but ignoring such an alert was contrary to the policy of the institution, the human reviewer may determine to manually issue a follow-up alert to the clinician. Thus, in some embodiments, an automatic fact review system may coexist in an institutional setting with a manual review process involving a human user, and the manual review process may provide back-up and/or additional functionality to complement the automatic fact review processes.

In some embodiments, when clinical facts are extracted from a free-form narration, a CLU engine may encounter situations in which disambiguation is desired between multiple facts that could potentially be extracted from the same portion of the free-form narration. For example, a term in the free-form narration might be linked to two different concepts in the formal ontology used by the CLU engine, and it might not be likely that both of those concepts were intended to coexist in the free-form narration. In such situations, a fact review system in some embodiments may provide a structured choice to the user to disambiguate between multiple facts tentatively extracted by the CLU engine. In some embodiments, each of the options provided in the structured choice may correspond to one of the multiple tentative facts, and the user may choose one of the options to specify which fact should actually be extracted from the free-form narration.

In some embodiments, when the user makes a selection of a fact presented through a structured choice provided by the fact review system, a textual representation of the clinician's free-form narration may automatically be updated to explicitly identify the selected fact as having been ascertained from the patient encounter. For example, if the free-form narration originally included a term linked to two different concepts in the CLU engine's ontology, the fact review system could present the user a structured choice between a different term linked only to one of the concepts and a different term linked only to the other of the concepts. When the user selects one of the different terms in the structured choice presented, in some embodiments the text narrative may automatically be updated to replace the original term with the selected term. In some embodiments, such updating of the text narrative may be performed in response to any type of user selection of an option provided by the fact review system, corresponding to a clinical fact that could possibly be ascertained from the patient encounter. Some examples include disambiguating options, options corresponding to additional facts for increased specificity and options corresponding to unspecified diagnoses, as discussed above. In some embodiments, rather than replacing text in the narrative, new text corresponding to the selected fact may be generated and simply added to the narrative in one or more appropriate locations. In some embodiments, the location(s) at which to insert text identifying the selected fact may be automatically determined by identifying one or more section headings in the text narrative, and by inserting the text in the section or sections most closely corresponding to the selected fact.

In some embodiments, a fact review system may allow a clinician or other user to directly add a clinical fact as a discrete structured data item, and to indicate a linkage to a portion of the clinician's free-form narration of the patient encounter from which the added fact should have been extracted. For example, the user may specify a clinical fact as a discrete structured data element, select a word or set of words (which need not be contiguous) in the free-form narration, and indicate that the specified fact is ascertained from that portion (e.g., that word or set of words) of the free-form narration. In some embodiments, when such a fact is added, the CLU engine may be updated for that user (or for the clinician who provided the free-form narration) to link the selected word(s) from the free-form narration to one or more concepts in the formal ontology corresponding to the added fact. In some embodiments, the free-form narration may further be re-processed by the updated CLU engine to extract any further additional facts that may be determined based on the updated terminology. In one example, if the user selected a word in the patient history section of the free-form narration, and added a fact specifying that the patient has a history of a particular condition, the updated CLU engine re-processing the free-form narration might identify the same word in the family history section, and extract an additional fact that the patient has a family history of the same condition. In some embodiments, such automatic re-processing may spare the clinician or other user the time and effort that otherwise would be required to define multiple facts corresponding to the same terminology in the free-form dictation. In some embodiments, similar re-processing may be performed when the user edits or deletes a fact originally extracted automatically from the free-form narration, when the fact is linked to terminology that appears in multiple parts of the free-form narration.

In some embodiments, as discussed above, a fact review system may allow a user to add, delete and/or modify (collectively referred to as "change") a clinical fact extracted from a free-form narration of a patient encounter provided by a clinician, resulting in a change to the set of extracted facts. In some instances, one or more such changes made to the set of facts corresponding to the current patient encounter may create one or more inconsistencies between the set of facts and the semantic content of the original free-form narration. For example, a clinician may originally specify a particular diagnosis in a free-form narration, and a CLU engine may extract a clinical fact corresponding to that diagnosis. If the clinician later changes his mind and would like to replace the original diagnosis with a different diagnosis, he may have the option in some embodiments of simply editing the extracted fact directly, rather than editing the data representation of the free-form narration itself. Such a situation may create an inconsistency between the free-form narration and the corresponding set of clinical facts, as the facts may now specify the new diagnosis, and the free-form narration may still specify the original diagnosis. In such situations, the fact review system in some embodiments may alert the clinician or other user to the inconsistency, and/or may provide any of several options to the user to address the inconsistency. One option may be to ignore the inconsistency and allow it to persist in the clinical documentation. Another option may be to allow the user to edit the data representation of the free-form narration to be consistent with the current set of clinical facts. Another option may be to allow the system to automatically update the data representation of the free-form narration by adding, deleting or replacing one or more portions of the free-form narration. Yet another option may be simply to append a note to the free-form narration, indicating and optionally explaining the inconsistency.

In some embodiments, as discussed above, a clinical fact review system may provide various tools for a clinician to review and/or edit facts corresponding to a current patient encounter, receive alerts generated based on those facts, review and/or edit a free-form narration of the patient encounter provided by the clinician, and/or review the linkages maintained between clinical facts extracted by a CLU engine and the portions of the free-form narration from which the clinical facts were extracted. Such tools may be provided in any suitable form, including visual forms, audio forms, combined forms or any other form providing the functionality described herein, as aspects of the present invention are not limited in this respect. When the tools are provided in visual form, their functionality may be accessed through a graphical user interface (GUI). In some embodiments, the GUI may be organized in a way to allow the human user(s) to efficiently process the information displayed. For example, in some embodiments, text narratives, facts and alerts may be displayed in consistent locations within the user interface and organized by type and/or priority. Different colors, textual styles and/or graphical styles may be utilized to direct the user's attention to high-priority alerts, and/or to make linkages between related items in the display easily recognizable. In some embodiments, the organization and/or composition of such a visual display may be determined in accordance with principles used in the development of heads-up displays (HUDs).

In some embodiments, a fact review system operating on a set of clinical facts ascertained from a patient encounter may provide tools for promoting efficiency in the workflow of the clinician and/or other personnel beyond the conclusion of the patient encounter. For example, in some embodiments, the fact review system may interface with one or more Computerized Physician Order Entry (CPOE) systems to automatically place orders for prescriptions, laboratory tests, radiology screenings, surgical or other medical procedures and/or other planned treatment action items, based on such items (e.g., medication names, dosages, procedure names, dates, etc.) being specified in the set of facts corresponding to the current patient encounter. In some embodiments, such items may be identified based on their being extracted from a "plan" section of a free-form narration. In some embodiments, the fact review system may interface with one or more scheduling systems to schedule appointments for medical procedures and/or future office visits within or external to the institution. In some embodiments, the fact review system may format one or more facts into a standard or proprietary messaging format to facilitate interfacing with any of such systems. In some embodiments, billing reports, patient discharge instructions and/or other documents may be automatically generated or initially populated based on the set of clinical facts. In some embodiments with any of the above-described functionality, the fact review system may provide an alert to the user and/or may prompt for user or clinician approval prior to taking any of the above actions.

In some embodiments, a fact review system may provide tools for evidence-based clinical decision support based on the set of clinical facts collected for the current patient encounter. In some embodiments, the fact review system may have access to one or more data sets of past patient reports and/or one or more archives of medical literature documents that may provide information regarding various conditions, treatment outcomes and the like that are relevant to the current patient encounter. In some embodiments, the available documents may have been processed by the CLU engine and indexed using the same system of terminology used to extract clinical facts from free-form clinical narrations. As such, in some embodiments, the facts corresponding to the current patient encounter may be efficiently matched to relevant available documents, and those documents or a subset thereof may be retrieved for display or otherwise provided to the clinician to aid in his determination of a treatment plan for the current patient. In some embodiments, a statistical model may be trained on the data set of past patient outcomes and/or on data in the medical literature, such that the system may go beyond mere presentation of references to actually predict best courses of treatment by applying the statistical model to the collection of facts corresponding to the current patient encounter and/or to the patient's medical history. In some embodiments, treatment recommendations may be provided to the clinician along with links to references in the literature or other available data supporting the recommendations. In some embodiments, CLU indexing of large quantities of patient records and/or literature documents may also be used to facilitate clinical research studies, as available natural language documents may be efficiently mapped to an ad hoc query corresponding to a research question. From the resulting corpus of conceptually relevant documents, treatment outcomes and/or other required information or facts may be extracted using CLU technology to aid in synthesizing an answer to the research question.

While a number of inventive features for clinical documentation processes are described above, it should be appreciated that embodiments of the present invention may include any one of these features, any combination of two or more features, or all of the features, as aspects of the invention are not limited to any particular number or combination of the above-described features. The aspects of the present invention described herein can be implemented in any of numerous ways, and are not limited to any particular implementation techniques. Described below are examples of specific implementation techniques; however, it should be appreciate that these examples are provided merely for purposes of illustration, and that other implementations are possible.

One illustrative application for the techniques described herein is for use in a system for enhancing clinical documentation processes. An exemplary operating environment for such a system is illustrated in FIG. 1. The exemplary operating environment includes a server 100 communicatively connected via any suitable communication medium or media (e.g., local and/or network connections) to terminals 110 and 140. Server 100 and terminals 110 and 140 each may be implemented in any suitable form, as aspects of the present invention are not limited in this respect. For example, each may be implemented as a single stand-alone machine, or may be implemented by multiple distributed machines that share processing tasks in any suitable manner. Any or all of the machines designated as server 100 and terminals 110 and 140 may be implemented as one or more computers; an example of a suitable computer is described below. In some embodiments, each of server 100 and terminals 110 and 140 may include one or more non-transitory computer-readable storage devices storing processor-executable instructions, and one or more processors that execute the processor-executable instructions to perform the functions described herein. The storage devices may be implemented as computer-readable storage media encoded with the processor-executable instructions; examples of suitable computer-readable storage media are discussed below.

As depicted, server 100 includes an ASR engine 102, a CLU engine 104, and a fact review component 106. Each of these processing components of server 100 may be implemented in software, hardware, or a combination of software and hardware. Components implemented in software may comprise sets of processor-executable instructions that may be executed by the one or more processors of server 100 to perform the functionality described herein. Each of ASR engine 102, CLU engine 104 and fact review component 106 may be implemented as a separate component of server 100, or any combination of these components may be integrated into a single component or a set of distributed components. In addition, any one of ASR engine 102, CLU engine 104 and fact review component 106 may be implemented as a set of multiple software and/or hardware components. It should be understood that any such component depicted in FIG. 1 is not limited to any particular software and/or hardware implementation and/or configuration.

As illustrated in FIG. 1, terminal 110 is operated by a clinician 120, who may be a physician, a physician's aide, a nurse, or any other personnel involved in the evaluation and/or treatment of a patient 122 in a clinical setting. During the course of a clinical encounter with patient 122, or at some point thereafter, clinician 120 may wish to document the patient encounter. Such a patient encounter may include any interaction between clinician 120 and patient 122 in a clinical evaluation and/or treatment setting, including, but not limited to, an office visit, an interaction during hospital rounds, an outpatient or inpatient procedure (surgical or non-surgical), a follow-up evaluation, a visit for laboratory or radiology testing, etc. One method that clinician 120 may use to document the patient encounter may be to enter clinical facts that can be ascertained from the patient encounter into terminal 110 as discrete structured data items. The set of clinical facts, once entered, may be transmitted in some embodiments via any suitable communication medium or media (e.g., local and/or network connection(s) that may include wired and/or wireless connection(s)) to server 100. Specifically, in some embodiments, the set of clinical facts may be received at server 100 by a fact review component 106, exemplary functions of which are described below.

Another method that may be used by clinician 120 to document the patient encounter is to provide a free-form narration of the patient encounter. In some embodiments, the narration may be free-form in the sense that clinician 120 may be unconstrained with regard to the structure and content of the narration, and may be free to provide any sequence of words, sentences, paragraphs, sections, etc., that he would like. In some embodiments, there may be no limitation on the length of the free-form narration, or the length may be limited only by the processing capabilities of the user interface into which it is entered or of the later processing components that will operate upon it. In other embodiments, the free-form narration may be constrained in length (e.g., limited to a particular number of characters).

A free-form narration of the patient encounter may be provided by clinician 120 in any of various ways. One way may be to manually enter the free-form narration in textual form into terminal 110, e.g., using a keyboard. In this respect, the one or more processors of terminal 110 may in some embodiments be programmed to present a user interface including a text editor/word processor to clinician 120. Such a text editor/word processor may be implemented in any suitable way, as aspects of the present invention are not limited in this respect.

Another way to provide a free-form narration of the patient encounter may be to verbally speak a dictation of the patient encounter. Such a spoken dictation may be provided in any suitable way, as aspects of the present invention are not limited in this respect. As illustrated in FIG. 1, one way that clinician 120 may provide a spoken dictation of the free-form narration may be to speak the dictation into a microphone 112 operatively connected (e.g., via a direct wired connection, a direct wireless connection, or via a connection through an intermediate device) to terminal 110. An audio recording of the spoken dictation may then be stored in any suitable data format, and transmitted to server 100. Another way that clinician 120 may provide the spoken dictation may be to speak into a telephone 118, from which an audio signal may be transmitted to be recorded at server 100, at the site of medical transcriptionist 130, or at any other suitable location. Alternatively, the audio signal may be recorded in any suitable data format at an intermediate facility, and the audio data may then be relayed to server 100 or to medical transcriptionist 130.

In some embodiments, medical transcriptionist 130 may receive the audio recording of the dictation provided by clinician 120, and may transcribe it into a textual representation of the free-form narration (e.g., into a text narrative). Medical transcriptionist 130 may be any human who listens to the audio dictation and writes or types what was spoken into a text document. In some embodiments, medical transcriptionist 130 may be specifically trained in the field of medical transcription, and may be well-versed in medical terminology. In some embodiments, medical transcriptionist 130 may transcribe exactly what she hears in the audio dictation, while in other embodiments, medical transcriptionist 130 may add formatting to the text transcription to comply with generally accepted medical document standards. When medical transcriptionist 130 has completed the transcription of the free-form narration into a textual representation, the resulting text narrative may in some embodiments be transmitted to server 100 or any other suitable location (e.g., to a storage location accessible to server 100). Specifically, in some embodiments the text narrative may be received from medical transcriptionist 130 by CLU engine 104 within server 100. Exemplary functionality of CLU engine 104 is described below.

In some other embodiments, the audio recording of the spoken dictation may be received, at server 100 or any other suitable location, by automatic speech recognition (ASR) engine 102. In some embodiments, ASR engine 102 may then process the audio recording to determine what was spoken. As discussed above, such processing may involve any suitable speech recognition technique, as aspects of the present invention are not limited in this respect. In some embodiments, the audio recording may be automatically converted to a textual representation, while in other embodiments, words identified directly from the audio recording may be represented in a data format other than text, or abstract concepts may be identified instead of words. Examples of further processing are described below with reference to a text narrative that is a textual representation of the free-form narration; however, it should be appreciated that similar processing may be performed on other representations of the free-form narration as discussed above. When a textual representation is produced, in some embodiments it may be reviewed by a human (e.g., a transcriptionist) for accuracy, while in other embodiments the output of ASR engine 102 may be accepted as accurate without human review.

In some embodiments, ASR engine 102 may make use of a lexicon of clinical terms (which may be part of, or in addition to, another more general speech recognition lexicon) while determining the sequence of words that were spoken in the free-form narration provided by clinician 120. However, aspects of the invention are not limited to the use of a lexicon, or any particular type of lexicon, for ASR. When used, the clinical lexicon in some embodiments may be linked to a clinical language understanding ontology utilized by CLU engine 104, such that ASR engine 102 might produce a text narrative containing terms in a form understandable to CLU engine 104. In some embodiments, a more general speech recognition lexicon might also be shared between ASR engine 102 and CLU engine 104. However, in other embodiments, ASR engine 102 may not have any lexicon intentionally in common with CLU engine 104. In some embodiments, a lexicon used by ASR engine 102 may be linked to a different type of clinical ontology, such as one not designed or used for language understanding. It should be appreciated that any lexicon used by ASR engine 102 and/or CLU engine 104 may be implemented and/or represented as data in any suitable way, as aspects of the invention are not limited in this respect.

In some embodiments, a text narrative, whether produced by ASR engine 102 (and optionally verified or not by a human), produced by medical transcriptionist 130, directly entered in textual form through terminal 110, or produced in any other way, may be re-formatted in one or more ways before being received by CLU engine 104. Such re-formatting may be performed by ASR engine 102, by a component of CLU engine 104, by a combination of ASR engine 102 and CLU engine 104, or by any other suitable software and/or hardware component. In some embodiments, the re-formatting may be performed in a way known to facilitate fact extraction, and may be performed for the purpose of facilitating the extraction of clinical facts from the text narrative by CLU engine 104. For example, in some embodiments, processing to perform fact extraction may be improved if sentence boundaries in the text narrative are accurate. Accordingly, in some embodiments, the text narrative may be re-formatted prior to fact extraction to add, remove or correct one or more sentence boundaries within the text narrative. In some embodiments, this may involve altering the punctuation in at least one location within the text narrative. In another example, fact extraction may be improved if the text narrative is organized into sections with headings, and thus the re-formatting may include determining one or more section boundaries in the text narrative and adding, removing or correcting one or more corresponding section headings. In some embodiments, the re-formatting may include normalizing one or more section headings (which may have been present in the original text narrative and/or added or corrected as part of the re-formatting) according to a standard for the healthcare institution corresponding to the patient encounter (which may be an institution-specific standard or a more general standard for section headings in clinical documents). In some embodiments, a user (such as clinician 120, medical transcriptionist 130, or another user) may be prompted to approve the re-formatted text.

Any suitable technique(s) for implementing re-formatting, examples of which are described above, may be employed, as aspects of the invention are not limited in this respect. One exemplary technique suitable for performing re-formatting of a text narrative is described in U.S. patent application Ser. No. 11/322,971, filed on Dec. 30, 2005, entitled "Translating Literal Speech to Formatted Text", which is incorporated herein by reference in its entirety. Another exemplary technique that may be used in some embodiments for performing re-formatting of a text narrative involves the use of word N-gram statistical models to predict sentence and/or section boundaries in a text narrative. Such statistical models may be trained on a corpus of documents (e.g., past medical records) with correct punctuation and/or section headings (e.g., supplied by a medical transcriptionist).

In some embodiments, a statistical model may add punctuation (e.g., periods, exclamation points, question marks, etc.) to add one or more sentence boundaries to a text narrative by computing a probability, for each word in the text narrative, that a particular punctuation mark should follow that word. In computing the probability that a word should be followed by a punctuation mark, the statistical model may consider the N-word sequence from the text narrative that ends with that word, and determine the frequency with which that N-word sequence is followed by that punctuation mark in the training data for the statistical model. A lattice may then be constructed using the computed probabilities for all the words in the text narrative, or in a portion of the text narrative, and the best path in terms of combined probability through the lattice may be determined. Where punctuation marks are located in the best path through the lattice, those punctuation marks may be added in those locations to the text narrative in producing the formatted text. In some embodiments, another statistical model may add section headings, corresponding to section boundaries, in a similar fashion. For example, in some embodiments, a statistical model for section headings may compute probabilities, for each word, that the word should be followed by a section boundary. In some embodiments, in computing probabilities, a statistical model for section headings may consider more words that follow the current word than words that precede the current word. In some embodiments, one or more separate statistical models may be trained to delete incorrect sentence and/or section boundaries. Those models in some embodiments may be trained through feedback from clinician 120 or another user, by observing word sequences (initially including punctuation and/or section boundaries) from which clinician 120 or another user tends to remove the punctuation and/or section boundaries when editing.

In some embodiments, either an original or a re-formatted text narrative may be received by CLU engine 104, which may perform processing to extract one or more clinical facts from the text narrative. The text narrative may be received from ASR engine 102, from medical transcriptionist 130, directly from clinician 120 via terminal 110, or in any other suitable way. Any suitable technique(s) for extracting clinical facts from the text narrative may be used, as aspects of the present invention are not limited in this respect. Exemplary techniques for clinical fact extraction are described above, and may involve the use of a clinical language understanding ontology with concepts linked to a lexicon of clinical terms.

In some embodiments, a user such as clinician 120 may monitor, control and/or otherwise interact with the fact extraction and/or fact review process through a user interface provided in connection with server 100. One exemplary implementation of such a user interface is graphical user interface (GUI) 200, illustrated in FIG. 2. In some embodiments, when the user is clinician 120, GUI 200 may be presented on a visual display 114 of terminal 110, and data displayed via GUI 200 may be downloaded to terminal 110 from server 100. In some embodiments, a user may be person other than a clinician; for example, another person such as coding specialist 150 may be presented with GUI 200 via visual display 144 of terminal 140. However, the user interface is not limited to a graphical user interface, as other ways of providing data to users from server 100 may be used. For example, in some embodiments, audio indicators may be transmitted from server 100 and conveyed to a user (e.g., via speaker 116 and/or speaker 146). It should be appreciated that any type of user interface may be provided in connection with fact extraction, fact review and/or other related processes, as aspects of the invention are not limited in this respect. While exemplary embodiments as illustrated in FIG. 1 involve data processing at server 100 and data communication between server 100 and terminals 110 and/or 140, it should be appreciated that in other embodiments any or all processing components of server 100 may instead be implemented locally at terminal 110 and/or terminal 140, as aspects of the invention are not limited to any particular distribution of local and/or remote processing capabilities.

As depicted in FIG. 2, GUI 200 includes a number of separate panes displaying different types of data. Identifying information pane 210 includes general information identifying patient 222 as a male patient named John Doe. Such general patient identifying information may be entered by clinician 120, or by other user 150, or may be automatically populated from an electronic medical record for patient 122, or may be obtained from any other suitable source. Identifying information pane 210 also displays the creation date and document type of the report currently being worked on. This information may also be obtained from any suitable source, such as from stored data or by manual entry. When referring herein to entry of data by clinician 120 and/or other user 150, it should be appreciated that any suitable form of data entry may be used, including input via mouse, keyboard, touchscreen, stylus, voice, or any other suitable input form, as aspects of the invention are not limited in this respect.

GUI 200 as depicted in FIG. 2 includes a text panel 220 in which a text narrative referring to the encounter between clinician 120 and patient 122 is displayed. In some embodiments, text panel 220 may include text editor functionality, such that clinician 120 may directly enter the text narrative into text panel 220, either during the patient encounter or at some time thereafter. If ASR is used to produce the text narrative from a spoken dictation provided by clinician 120, in some embodiments the text may be displayed in text panel 220 as it is produced by ASR engine 102, either in real time while clinician 120 is dictating, or with a larger processing delay. In other embodiments, the text narrative may be received as stored data from another source, such as from medical transcriptionist 130, and may be displayed in completed form in text panel 220. In some embodiments, the text narrative may then be edited if desired by clinician 120 and/or other user 150 within text panel 220. However, text editing capability is not required, and in some embodiments text panel 220 may simply display the text narrative without providing the ability to edit it.

Exemplary GUI 200 further includes a fact panel 230 in which one or more clinical facts, once extracted from the text narrative and/or entered in another suitable way, may be displayed as discrete structured data items. When clinician 120 and/or other user 150 is ready to direct CLU engine 104 to extract one or more clinical facts from the text narrative, in some embodiments he or she may select process button 240 via any suitable selection input method. However, a user indication to begin fact extraction is not limited to a button such as process button 240, as any suitable way to make such an indication may be provided by GUI 200. In some embodiments, no user indication to begin fact extraction may be required, and CLU engine 104 may begin a fact extraction process as soon as a requisite amount of text (e.g., enough text for CLU engine 104 to identify one or more clinical facts that can be ascertained therefrom) is entered and/or received. In some embodiments, a user may select process button 240 to cause fact extraction to be performed before the text narrative is complete. For example, clinician 120 may dictate, enter via manual input and/or otherwise provide a part of the text narrative, select process button 240 to have one or more facts extracted from that part of the text narrative, and then continue to provide further part(s) of the text narrative. In another example, clinician 120 may provide all or part of the text narrative, select process button 240 and review the resulting extracted facts, edit the text narrative within text pane 220, and then select process button 240 again to review how the extracted facts may change.

Figure 3B:
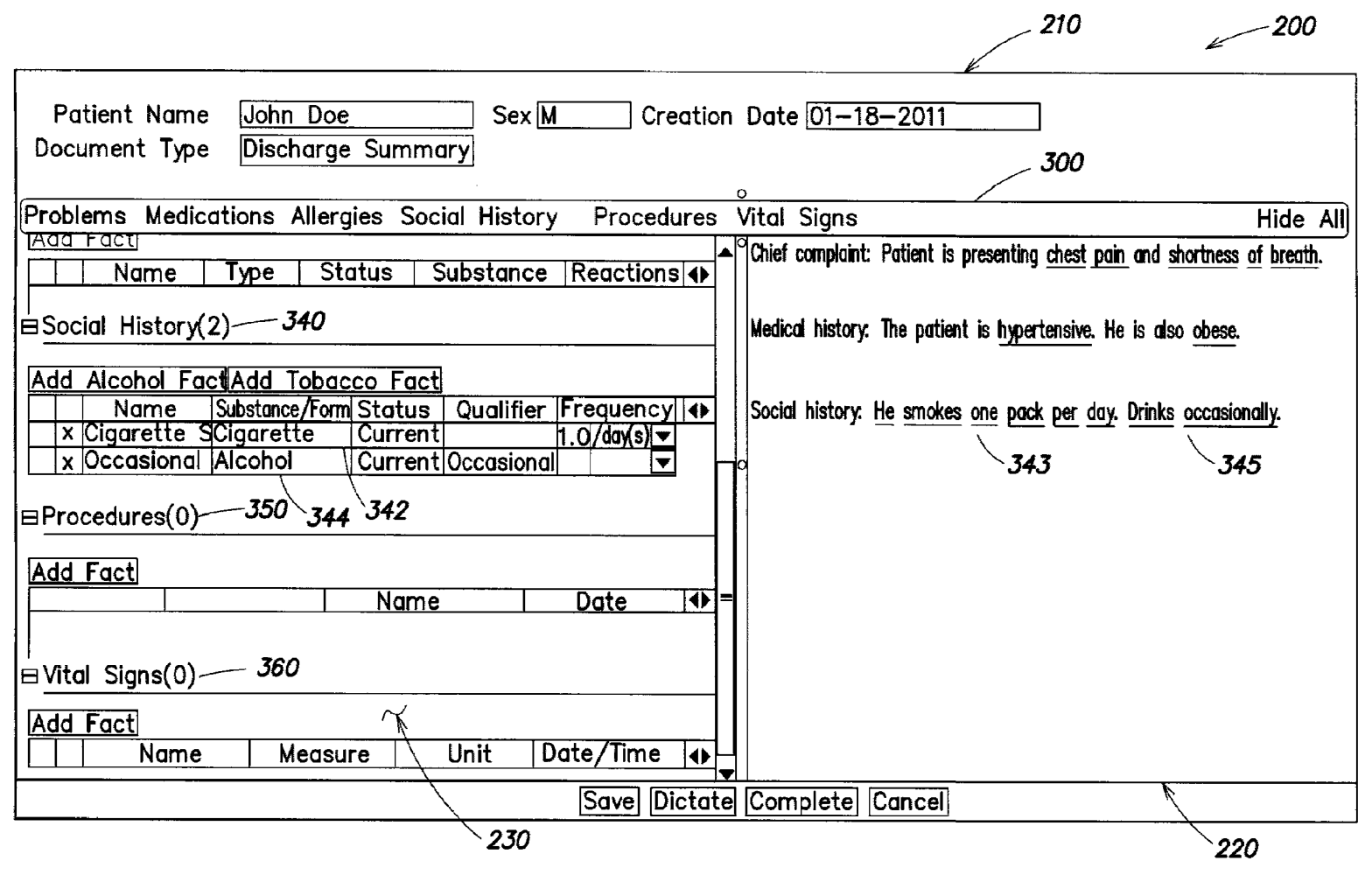

In some embodiments, one or more clinical facts extracted from the text narrative by CLU engine 104 may be displayed to the user via GUI 200 in fact panel 230. Screenshots illustrating an example display of clinical facts extracted from an example text narrative are provided in FIGS. 3A and 3B. FIG. 3A is a screenshot with fact panel 230 scrolled to the top of a display listing clinical facts extracted from the example text narrative, and FIG. 3B is a screenshot with fact panel 230 scrolled to the bottom of the display listing the extracted clinical facts. In some embodiments, as depicted in FIGS. 3A and 3B, clinical facts corresponding to a patient encounter may be displayed in fact panel 230, and organized into a number of separate categories of types of facts. An exemplary set of clinical fact categories includes categories for problems, medications, allergies, social history, procedures and vital signs. However, it should be appreciated that any suitable fact categories may be used, as aspects of the invention are not limited in this respect. In addition, organization of facts into categories is not required, and displays without such organization are possible. As depicted in FIGS. 3A and 3B, in some embodiments GUI 200 may be configured to provide a navigation panel 300, with a selectable indication of each fact category available in the display of fact panel 230. In some embodiments, when the user selects one of the categories within navigation panel 300 (e.g., by clicking on it with a mouse, touchpad, stylus, or other input device), fact panel 230 may be scrolled to display the corresponding fact category. As depicted in FIGS. 3A and 3B, all available fact categories for the current document type are displayed, even if a particular fact category includes no extracted or otherwise entered clinical facts. However, this is not required; in some embodiments, only those fact categories having facts ascertained from the patient encounter may be displayed in fact panel 230.

Fact panel 230 scrolled to the top of the display as depicted in FIG. 3A shows problem fact category 310, medications fact category 320, and allergies fact category 330. Within problem fact category 310, four clinical facts have been extracted from the example text narrative; no clinical facts have been extracted in medications fact category 320 or in allergies fact category 330. Within problem fact category 310, fact 312 indicates that patient 122 is currently presenting with unspecified chest pain; that the chest pain is a currently presenting condition is indicated by the status "active". Fact 314 indicates that patient 122 is currently presenting with shortness of breath. Fact 316 indicates that the patient has a history (status "history") of unspecified essential hypertension. Fact 318 indicates that the patient has a history of unspecified obesity. As illustrated in FIG. 3A, each clinical fact in problem fact category 310 has a name field and a status field. In some embodiments, each field of a clinical fact may be a structured component of that fact represented as a discrete structured data item. In this example, the name field may be structured such that only a standard set of clinical terms for problems may be available to populate that field. For example, the status field may be structured such that only statuses in the Systematized Nomenclature of Medicine (SNOMED) standard (e.g., "active" and "history") may be selected within that field, although other standards (or no standard) could be employed. An exemplary list of fact categories and their component fields is given below. However, it should be appreciated that this list is provided by way of example only, as aspects of the invention are not limited to any particular organizational system for facts, fact categories and/or fact components.

Exemplary List of Fact Categories and Component Fields

Category: Problems. Fields: Name, SNOMED status, ICD code.

Category: Medications. Fields: Name, Status, Dose form, Frequency, Measures, RxNorm code, Administration condition, Application duration, Dose route.

Category: Allergies. Fields: Allergen name, Type, Status, SNOMED code, Allergic reaction, Allergen RxNorm.

Category: Social history—Tobacco use. Fields: Name, Substance, Form, Status, Qualifier, Frequency, Duration, Quantity, Unit type, Duration measure, Occurrence, SNOMED code, Norm value, Value.

Category: Social history—Alcohol use. Fields: Name, Substance, Form, Status, Qualifier, Frequency, Duration, Quantity, Quantifier, Unit type, Duration measure, Occurrence, SNOMED code, Norm value, Value.

Category: Procedures. Fields: Name, Date, SNOMED code.

Category: Vital signs. Fields: Name, Measure, Unit, Unit type, Date/Time, SNOMED code, Norm value, Value.

In some embodiments, a linkage may be maintained between one or more clinical facts extracted by CLU engine 104 and the portion(s) of the text narrative from which they were extracted. As discussed above, such a portion of the text narrative may consist of a single word or may include multiple words, which may be in a contiguous sequence or may be separated from each other by one or more intervening words, sentence boundaries, section boundaries, or the like. For example, fact 312 indicating that patient 122 is currently presenting with unspecified chest pain may have been extracted by CLU engine 104 from the words "chest pain" in the text narrative. The "active" status of extracted fact 312 may have been determined by CLU engine 104 based on the appearance of the words "chest pain" in the section of the text narrative with the section heading "Chief complaint". In some embodiments, CLU engine 104 and/or another processing component may be programmed to maintain (e.g., by storing appropriate data) a linkage between an extracted fact (e.g., fact 312) and the corresponding text portion (e.g., "chest pain").

In some embodiments, GUI 200 may be configured to provide visual indicators of the linkage between one or more facts displayed in fact panel 230 and the corresponding portion(s) of the text narrative in text panel 220 from which they were extracted. In the example depicted in FIG. 3A, the visual indicators are graphical indicators consisting of lines placed under the appropriate portions of the text narrative in text panel 220. Indicator 313 indicates the linkage between fact 312 and the words "chest pain" in the "Chief complaint" section of the text narrative; indicator 315 indicates the linkage between fact 314 and the words "shortness of breath" in the "Chief complaint" section of the text narrative; indicator 317 indicates the linkage between fact 316 and the word "hypertensive" in the "Medical history" section of the text narrative; and indicator 319 indicates the linkage between fact 318 and the word "obese" in the "Medical history" section of the text narrative. However, these are merely examples of one way in which visual indicators may be provided, as other types of visual indicators may be provided. For example, different or additional types of graphical indicators may be provided, and/or linked text in text panel 220 may be displayed in a distinctive textual style (e.g., font, size, color, formatting, etc.). Aspects of the invention are not limited to any particular type of linkage indicator.

In some embodiments, when the textual representation of the free-form narration provided by clinician 120 has been re-formatted and fact extraction has been performed with reference to the re-formatted version, the original version may nevertheless be displayed in text panel 220, and linkages may be maintained and/or displayed with respect to the original version. For example, in some embodiments, each extracted clinical fact may be extracted by CLU engine 104 from a corresponding portion of the re-formatted text, but that portion of the re-formatted text may have a corresponding portion of the original text of which it is a formatted version. A linkage may therefore be maintained between that portion of the original text and the extracted fact, despite the fact actually having been extracted from the re-formatted text. In some embodiments, providing an indicator of the linkage between the extracted fact and the original text may allow clinician 120 and/or other user 150 to appreciate how the extracted fact is related to what was actually said in the free-form narration. However, other embodiments may maintain linkages between extracted facts and the re-formatted text, as an alternative or in addition to the linkages between the extracted facts and the original text, as aspects of the invention are not limited in this respect.

Fact panel 230 scrolled to the bottom of the display as depicted in FIG. 3B shows social history fact category 340, procedures fact category 350, and vital signs fact category 360. Within social history fact category 340, two clinical facts have been extracted; no facts have been extracted in procedures fact category 350 and vital signs fact category 360. Within social history fact category 340, fact 342 indicates that patient 122 currently smokes cigarettes with a frequency of one pack per day. Fact 344 indicates that patient 122 currently occasionally drinks alcohol. Indicator 343 indicates that fact 342 was extracted from the words "He smokes one pack per day" in the "Social history" section of the text narrative; and indicator 345 indicates that fact 344 was extracted from the words "Drinks occasionally" in the "Social history" section of the text narrative. In some embodiments, visual indicators such as indicators 343 and 345 may be of a different textual and/or graphical style or of a different indicator type than visual indicators such as indicators 313, 315, 317 and 319, to indicate that they correspond to a different fact category. For example, in some embodiments indicators 343 and 345 corresponding to social history fact category 340 may be displayed in a different color than indicators 313, 315, 317 and 319 corresponding to problems fact category 310. In some embodiments, linkages for different individual facts may be displayed in different textual and/or graphical styles or indicator types to allow the user to easily appreciate which fact corresponds to which portion of the text narrative. For example, in some embodiments indicator 343 may be displayed in a different color than indicator 345 because they correspond to different facts, even though both correspond to the same fact category.

Figure 4:
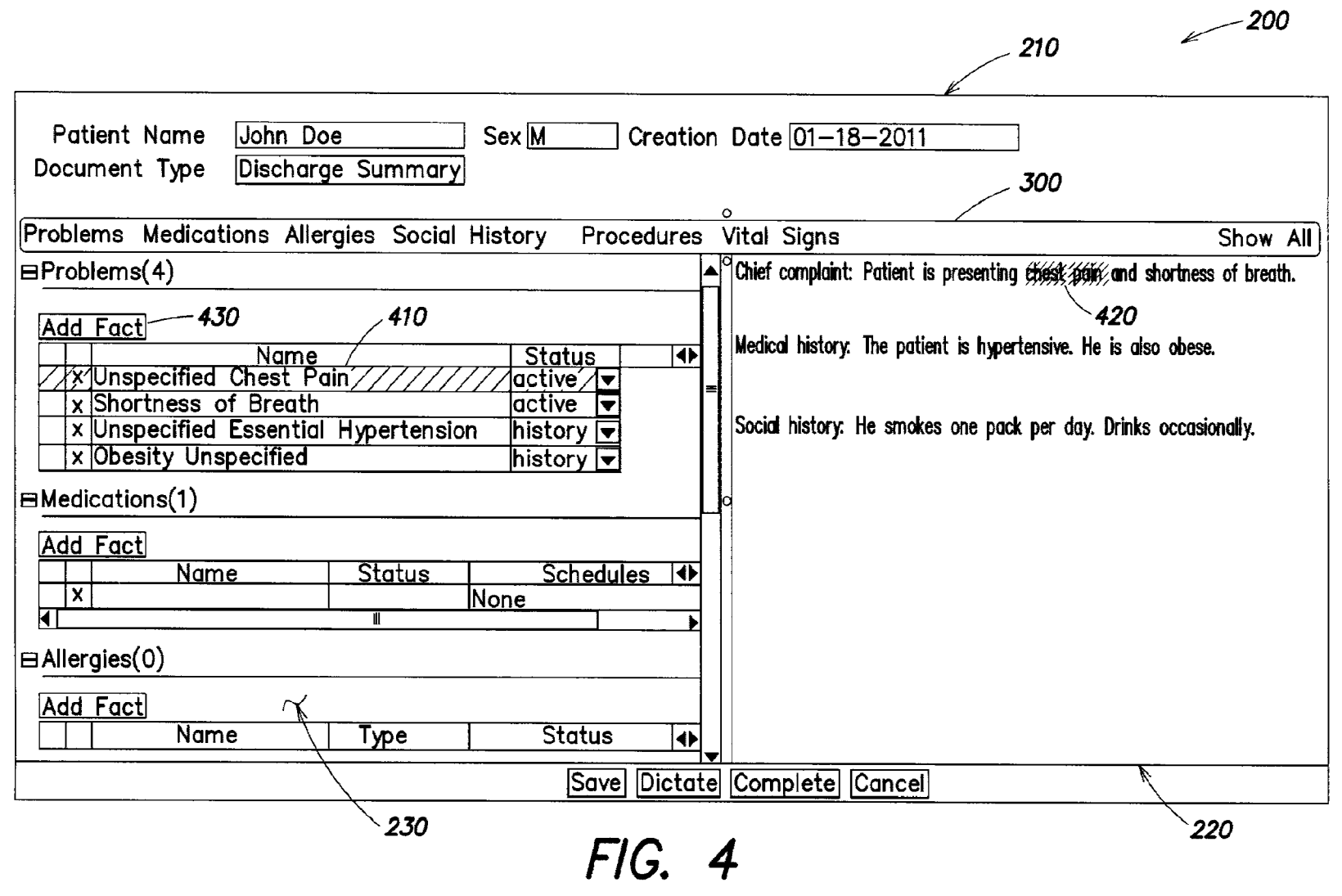

In some embodiments, GUI 200 may be configured to allow the user to select one or more of the clinical facts in fact panel 230, and in response to the selection, to provide an indication of the portion(s) of the text narrative from which those fact(s) were extracted. An example is illustrated in FIG. 4. In this example, fact 312 ("unspecified chest pain") has been selected by the user in fact panel 230, and in response visual indicator 420 of the portion of the text narrative from which fact 312 was extracted ("chest pain") is provided. Such a user selection may be made in any suitable way, as aspects of the invention are not limited in this respect. Examples include using an input device (e.g., mouse, keyboard, touchpad, stylus, etc.) to click on or otherwise select fact 312, hovering the mouse or other input mechanism above or nearby to fact 312, speaking a selection of fact 312 through voice, and/or any other suitable selection method. Similarly, in some embodiments GUI 200 may be configured to visually indicate the corresponding fact in fact panel 230 when the user selects a portion of the text narrative in text panel 220. In some embodiments, a visual indicator may include a line or other graphical connector between a fact and its corresponding portion of the text narrative. Any visual indicator may be provided in any suitable form (examples of which are given above) as aspects of the invention are not limited in this respect. In addition, aspects of the invention are not limited to visual indicators, as other forms of indicators may be provided. For example, in response to a user selection of fact 312, an audio indicator of the text portion "chest pain" may be provided in some embodiments. In some embodiments, the audio indicator may be provided by playing the portion of the audio recording of the clinician's spoken dictation comprising the words "chest pain". In other embodiments, the audio indicator may be provided by playing an audio version of the words "chest pain" generated using automatic speech synthesis. Any suitable form of indicator or technique for providing indicators may be used, as aspects of the invention are not limited in this respect.

In some embodiments, GUI 200 may be configured to provide any of various ways for the user to make one or more changes to the set of clinical facts extracted from the text narrative by CLU engine 104 and displayed in fact panel 230. For example, the user may be allowed to delete a fact from the set in fact panel 230, e.g., by selecting the "X" option appearing next to the fact. In some embodiments, the user may be allowed to edit a fact within fact panel 230. In one example, the user may edit the name field of fact 312 by selecting the fact and typing, speaking or otherwise providing a different name for that fact. As depicted in FIG. 3A and FIG. 4, in some embodiments the user may edit the status field of fact 312 by selecting a different status from the available drop-down menu, although other techniques for allowing editing of the status field are possible. In some embodiments, the user may alternatively or additionally be allowed to edit a fact by interacting with the text narrative in text panel 220. For example, the user may add, delete, or change one or more words in the text narrative, and then the text narrative may be re-processed by CLU engine 104 to extract an updated set of clinical facts. In some embodiments, the user may be allowed to select only a part of the text narrative in text panel 220 (e.g., by highlighting it), and have CLU engine 104 re-extract facts only from that part, without disturbing facts already extracted from other parts of the text narrative.

Figure 5:
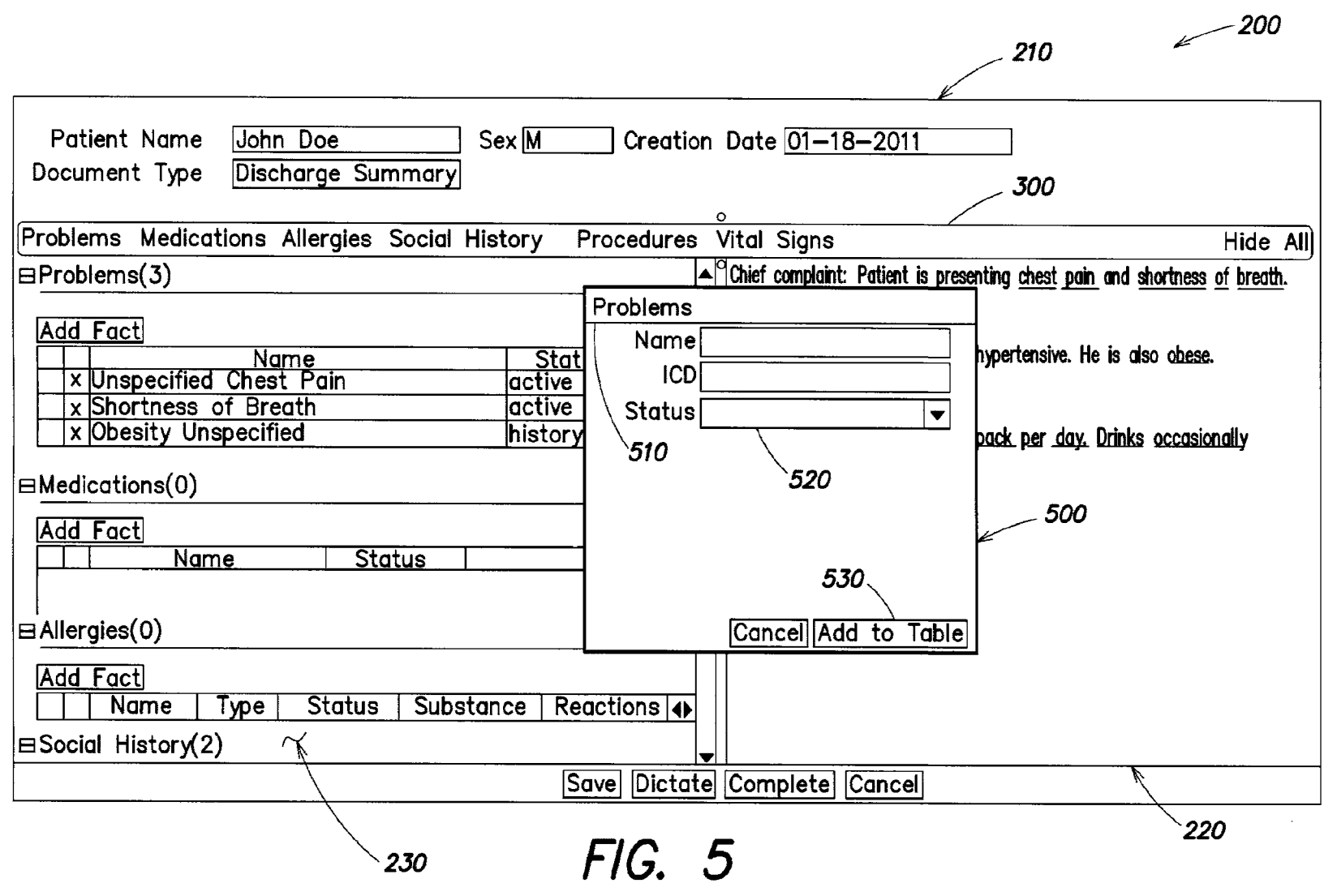

In some embodiments, GUI 200 may be configured to provide any of various ways for one or more facts to be added as discrete structured data items. As depicted in FIG. 4, GUI 200 in some embodiments may be configured to provide an add fact button for each fact category appearing in fact panel 230; one such add fact button is add fact button 430. When the user selects add fact button 430, in some embodiments GUI 200 may provide the user with a way to enter information sufficient to populate one or more fields of a new fact in that fact category, for example by displaying pop-up window 500 as depicted in FIG. 5. It should be appreciated that this is merely one example, as aspects of the invention are not limited to the use of pop-up windows or any other particular method for adding a fact. In this example, pop-up window 500 includes a title bar 510 that indicates the fact category ("Problems") to which the new fact will be added. Pop-up window 500 also provides a number of fields 520 in which the user may enter information to define the new fact to be added. Fields 520 may be implemented in any suitable form, including as text entry boxes, drop-down menus, radio buttons and/or checkboxes, as aspects of the invention are not limited to any particular way of receiving input defining a fact. Finally, pop-up window 500 includes add button 530, which the user may select to add the newly defined fact to the set of facts corresponding to the patient encounter, thus entering the fact as a discrete structured data item.

In some embodiments, GUI 200 may alternatively or additionally be configured to allow the user to add a new fact by selecting a (not necessarily contiguous) portion of the text narrative in text panel 220, and indicating that a new fact should be added based on that portion of the text narrative. This may be done in any suitable way. In one example, the user may highlight the desired portion of the text narrative in text panel 220, and right-click on it with a mouse (or perform another suitable input operation), which may cause the designated text to be processed and any relevant facts to be extracted. In other embodiments, the right-click or other input operation may cause a menu to appear. In some embodiments the menu may include options to add the new fact under any of the available fact categories, and the user may select one of the options to indicate which fact category will correspond to the new fact. In some embodiments, an input screen such as pop-up window 500 may then be provided, and the name field may be populated with the words selected by the user from the text narrative. The user may then have the option to further define the fact through one or more of the other available fields, and to add the fact to the set of clinical facts for the patient encounter as described above.

In some embodiments, the set of clinical facts corresponding to the current patient encounter (each of which may have been extracted from the text narrative or provided by the user as a discrete structured data item) may be added to an existing electronic medical record (such as an EHR) for patient 122, or may be used in generating a new electronic medical record for patient 122. In some embodiments, clinician 120 and/or coding specialist (or other user) 150 may finally approve the set of clinical facts before they are included in any patient record; however, aspects of the present invention are not limited in this respect. In some embodiments, when there is a linkage between a fact in the set and a portion of the text narrative, the linkage may be maintained when the fact is included in the electronic medical record. In some embodiments, this linkage may be made viewable by simultaneously displaying the fact within the electronic medical record and the text narrative (or at least the portion of the text narrative from which the fact was extracted), and providing an indication of the linkage in any of the ways described above. Similarly, extracted facts may be included in other types of patient records, and linkages between the facts in the patient records and the portions of text narratives from which they were extracted may be maintained and indicated in any suitable way.

In some embodiments, one or more clinical facts, either automatically extracted from a text narrative by CLU engine 104 or directly entered by a user as discrete structured data items, may be input to fact review component 106 for automatic review. In some embodiments, fact review component 106 may be programmed to identify opportunities for the clinical documentation of the patient encounter to be improved, and if any such opportunities are identified, to provide an alert to the user (e.g., clinician 120 or other user 150). Some examples of alerts that may be provided are described above. As discussed, any suitable form of alert, including visual and/or audio alerts, may be used, as aspects of the invention are not limited in this respect. In some embodiments, the review of collected clinical facts to determine opportunities for improved clinical documentation, and the resulting alerting and/or querying of the user, may be performed entirely automatically by fact review component 106 or any other suitable component. As used herein, performing a process "automatically" refers to having no required human participation between the input to the process and its corresponding output, with all intervening acts performed by machine.

As discussed above, one type of alert that may be provided to a user by fact review component 106 is an alert of a potential opportunity to increase the specificity of the set of facts ascertained from the patient encounter. This can be done in any suitable way. In some embodiments, fact review component may be programmed with a set of deterministic rules to decide when such a potential opportunity exists. For example, in some embodiments, if a clinical term corresponding to one of the facts is linked to a concept in the formal ontology used by CLU engine 104, and that concept is a parent to one or more more specific child concepts in the ontology, then fact review component 106 may generate an alert to query the user as to whether one of the more specific child concepts can actually be ascertained from the patient encounter. If the user answers in the affirmative, in some embodiments fact review component 106 may cause the more general fact to be replaced by a more specific version indicated by the user. Similarly, if one or more concepts in the formal ontology are linked to clinical terms appearing in the set of facts, and if those concepts have relationships in the ontology to a fact that could add specificity to the set of facts, and alert and/or query may be generated. As an example, if one or more conditions documented in the set of facts are known through ontological relationships to be symptoms of a specific diagnosis, in some embodiments fact review component 106 may query clinician 120 or other user 150 as to whether the specific diagnosis may be ascertained from the patient encounter and added to the facts. In some embodiments, as an alternative or in addition to the set of deterministic rules, a statistical model may be used to identify situations in which a potential opportunity to increase the specificity of the set of facts exists.

In another example, one or more of the facts in the set collected (either by fact extraction from a text narrative or by direct entry as one or more discrete structured data items) from the patent encounter may correspond to one or more standard codes used for billing, ordering, evaluating quality of care, or the like. Such standard codes may be specific to the healthcare institution or may be a standard shared by multiple institutions. Examples of such standard coding systems include, but are not limited to, ICD codes, CPT (Current Procedural Terminology) codes, E&M (Evaluation and Management) codes, MedDRA (Medical Dictionary for Regulatory Activities) codes, SNOMED codes, LOINC (Logical Observation Identifiers Names and Codes) codes, RxNorm codes, NDC (National Drug Code) codes and RadLex codes. Some such standard coding systems are hierarchical, in that certain codes within the system are more specific versions of other codes within the system. For example, in the ICD-10 coding system, code I20 represents "angina pectoris" (chest pain due to lack of blood and oxygen to the heart muscle). More specific versions of ICD-10 code I20 include I20.0 ("unstable angina"), I20.1 ("angina pectoris with documented spasm"), I20.8 ("other forms of angina pectoris") and I20.9 ("angina pectoris, unspecified"). In some embodiments, if one of the set of facts collected from the patient encounter includes a general-level code such as ICD-10 I20, fact review component 106 may be programmed to automatically query the user as to whether one of the corresponding specific-level codes could be ascertained from the patient encounter instead. In some embodiments, fact review component 106 may present the user with a structured choice among the available specific-level codes, and may allow the user to choose among the available options.

In another example, fact review component 106 may be programmed to alert the user when a specific fact may be implied by the combination of two or more facts appearing together in the set of facts collected from the patient encounter. One example is a set of facts that included a diagnosis of pneumonia as well as a test result indicating that pseudomonas was found in a sputum culture. Based on a deterministic rule, or a statistical model result, indicating that these two facts in combination may imply a more specific form of pneumonia due to the presence of an organism, fact review component 106 may query the user as to whether the more specific diagnosis can be ascertained from the patient encounter.

In some embodiments, an alert that would otherwise be generated from the current patient encounter may be suppressed if there is information in the patient's medical history that already provides the additional specificity. To this end, in some embodiments fact review component 106 may have access to a data set of patient history records 160 for patient 122, and may query patient history records 160 for such information prior to generating an alert to the user. For example, if the set of facts from the current patient encounter specifies a condition but does not specify whether it is "acute" or "chronic", but a previous record in patient history records 160 already specifies that the condition is "chronic", then fact review component 106 in some embodiments may automatically edit the set of facts for the current patient encounter to specify that the condition is "chronic", without bothering the user with an alert. However, in some embodiments, even if fact review component 106 can obtain such specificity enhancing information automatically, a message may still be generated to inform the user that the information is being automatically added, and to allow the user to reject the change if desired, or to ask the user to approve of the change being made.

In some embodiments, if it is a user 150, and not clinician 122, who responds to an alert to increase the specificity of a set of clinical facts for a patient encounter, clinician 120 may be prompted to approve any additional information provided by the other user 150 prior to finally approving the set of facts for the patient encounter. For example, in some embodiments user 150 may be a coding specialist who is assigned the task of reviewing and editing the set of clinical facts (which may include billing codes) into a version fit to be incorporated into an electronic medical record, patient reports, order forms, or other document types. In such a "back-end" arrangement, the set of clinical facts settled upon by coding specialist 150 may then in some embodiments be transmitted to clinician 120 to give final approval to the set of facts. In some other embodiments, coding specialist 150 may not be required. For example, in a "front-end" arrangement, clinician 120 may review and possibly edit the set of clinical facts himself, and finally approve the set of facts when he is satisfied. This may occur during the patient encounter in some embodiments, or at some time thereafter (e.g., before clinician 120 finally approves or signs off on the report) in other embodiments. In either type of arrangement, in some embodiments, processing by fact review component 106 or any other component to provide alerts, decision support, workflow tools or the like in relation to the set of facts may be performed prior to the clinician's final approval of the set of facts.

In some embodiments, similar processing may be performed by fact review component 106 to alert the user when it is determined that an unspecified diagnosis may possibly be ascertained from the patient encounter. As discussed above, examples of such unspecified diagnoses include comorbidities of one or more already specified diagnoses, and identification of one or more already specified diagnoses as complications of one or more other specified diagnoses and/or procedures. For example, if the set of facts collected for the patient encounter specified a diagnosis of pneumonia, and the patient's oxygen saturation is also low, it may be determined that respiratory failure, a comorbidity of pneumonia, may possibly be ascertained from the patient encounter. In such a case, fact review component 106 may generate an alert to the user. In some embodiments, such determinations may be made based on knowledge of best practices, with deterministic rules providing reminders of diagnoses that should be investigated, for best quality of care, when other related conditions are present. In other embodiments, such determinations may be made statistically, by inputting the collected set of facts and/or facts from the patient's medical history to a statistical model trained on past clinical reports and/or medical literature. In this way, patterns of diagnoses that tend to be related may be identified statistically, and alerts may be generated based on the likelihood that relationships observed in the past will surface in the current patient encounter. To this end, in some embodiments, fact review component 106 may have access to a data set of medical literature/documents 170 (such as past clinical reports from the healthcare institution and/or from other sources) from which statistical models may be built and updated.

In some embodiments, as discussed above, fact review component 106 may be programmed to generate an alert when it determines that two or more of the facts in the set collected from the patient encounter conflict with each other in some way, or when it determines that one or more of the facts in the set conflict with one or more facts in patient history records 160. In some embodiments, fact review component 106 may be programmed to automatically generate such alerts based on a known set of combinations of facts that have undesirable interactions. For example, an alert may be generated when the set of facts indicate that patient 122 has been prescribed a certain medication (drug A) in addition to a certain other medication (drug B) with which it negatively interacts, such that the two medications should not be prescribed together. In some embodiments, the prescriptions of both drug A and drug B may be specified in the set of facts collected from the current patient encounter, while in other embodiments, the prescription of drug A may be specified in a fact from the current patient encounter, and the prescription of drug B may be specified in a fact contained in patient history records 160. In some embodiments the known set of undesirable interactions may be represented in a data set locally accessible to fact review component 106, while in other embodiments, fact review component 106 may query one or more external data sets (such as those maintained by pharmacies) to determine whether given facts for patient 122 demonstrate any contraindications. In some embodiments, fact review component 106 or another suitable processing component may both maintain an internal data set and also query external data sets, for instance for periodic updates to the internal data set.

In some embodiments, an alert to a conflict may be triggered by a combination of facts, at least one of which does not correspond to a medication. For example, fact review component 106 may generate alerts for contraindications related to a combination of a medication with an allergy, a medication with a diagnosis, a medication with a patient's age or gender, a medication with a condition indicated in the patient's history, a medical procedure with any of the foregoing characteristics, or any other combination of a planned treatment with another clinical fact from the current patient encounter or from the patient's history for which the planned treatment is known to be contraindicated.

In some embodiments, as discussed above, fact review component 106 may generate an alert when it determines that there is an opportunity to add to the clinical documentation of the patient encounter for quality review purposes. In some embodiments, fact review component 106 may be programmed with a set of deterministic rules to generate automatic alerts in response to certain facts or certain combinations of facts, based on a standard set of quality of care measures. Such a quality of care standard may be proprietary and unique to the specific healthcare institution or may be a standard that is not institution specific, such as the PQRI standard or the JCAHO standard. Any suitable quality of care standard may be used, as aspects of the present invention are not limited to any particular quality of care standard. In some embodiments, when a collected fact or combination of facts is associated with a certain recommended action on the part of the clinician according to the quality of care standard, an alert may be provided to query the user as to whether the recommended action was performed. For example, if the set of facts specify that patient 122 is a smoker, in some embodiments fact review component 106 may generate an alert to remind clinician 120 to counsel patient 122 about quitting smoking, and to document the counseling in the patient record. In another example, if the set of facts specify that patient 122 presented with a heart attack, in some embodiments fact review component 106 may prompt clinician 120 to document how quickly aspirin was prescribed and/or administered, such that proof of compliance with the applicable quality of care standards may be documented. In some embodiments, fact review component 106 may be used to generate PQRI score reports, or the like, to send to insurance companies as compliance evidence to support reimbursement.

In some embodiments, as discussed above, fact review component 106 or another suitable component may generate an alert to the user when it determines that disambiguation is desired between multiple facts that could potentially be extracted from the same portion of the text narrative. For example, a term in the free-form narration might be linked to two different concepts in the formal ontology used by CLU engine 104, and it might not be likely that both of those concepts were intended to coexist in the free-form narration. For example, if the text narrative contains the word "cold", it may be difficult in some cases for CLU engine 104 to determine whether clinician 120 intended that word to mean that patient 122 is cold to the touch, that patient 122 has a runny nose, or that patient 122 has chronic obstructive lung disease (COLD). In such situations, fact review component 106 in some embodiments may provide a structured choice to the user to disambiguate between multiple facts tentatively extracted by CLU engine 104. In some embodiments, each of the options provided in the structured choice may correspond to one of the multiple tentative facts, and the user may choose one of the options to specify which fact should actually be extracted from the free-form narration. As discussed above, if the user choosing among the facts is a person other than clinician 120, such as coding specialist 150, then in some embodiments clinician 120 may be prompted to approve the user's choice before finally approving the set of facts for the patient encounter. In other embodiments, the user may be prompted to provide disambiguating information in free-form, rather than as a structured choice, as aspects of the invention relating to prompting for disambiguating information are not limited to any particular implementation.

In various situations, as discussed above, fact review component 106 may be programmed to generate an alert including a structured choice among a number of options corresponding to clinical facts that could possibly be ascertained from the patient encounter. Such a structured choice could include a choice among facts that could add specificity to a set of clinical facts already collected for the patient encounter, a choice among facts potentially implied by one or more combinations of facts already collected for the patient encounter, a choice to disambiguate between facts, or any other choice in which one or more structured options are presented to the user, from which the user may choose. Such a structured choice may be provided in any suitable way, including as a visual and/or audio listing of the options in the structured choice, as aspects of the invention are not limited in this respect. Similarly, the user's selection of an option from the structured choice may be received in any suitable way, including as manual input and/or spoken input, as aspects of the invention are not limited in this respect.

In some embodiments, in response to the user's selection of one of the options, fact review component 106 may, for example through use of CLU engine 104, perform an update to the text narrative to make it explicitly state information corresponding to the selected fact. For example, in some embodiments, CLU engine 104 may in a sense work backward from the selected fact to generate natural language text from which that fact could have been extracted in the forward sense. In some embodiments, the generated text may then be added to the text narrative. When the fact selected by the user through the structured choice is a replacement for or a disambiguation of a fact already extracted from the text narrative, the generated text may in some embodiments be used to replace the portion of the text narrative from which the original fact was extracted. In some embodiments, to determine where in the text narrative to add the generated text when no other text is to be replaced, CLU engine 104 may again work backward based on how the selected fact would have been extracted from the narrative. For example, in some embodiments CLU engine 104 may identify a section heading in the text narrative corresponding to the selected fact, and the generated text may be added to that section. (e.g., because a selected fact with a status of "history" would have been extracted from a section with a "history" heading, the corresponding generated text may be added to such a section in the text narrative.) In other embodiments, generated text may simply be added to a predetermined location in the text narrative, such as at the beginning or end of the narrative, regardless of the semantic content of the generated text.

In some embodiments, fact review component 106 may allow the user to specify a location in the text narrative where the generated text should be inserted, or may allow the user to correct the location initially determined automatically. In some embodiments, CLU engine 104 or another suitable component may be used to update the generated text in response to the user's indication of a new location at which to insert it in the text narrative. For example, based on whether the user selects a location that is sentence-initial, sentence-medial or sentence-final, or a location that is its own sentence or is within another sentence, the generated text may be adjusted in terms of capitalization, spacing, punctuation, etc., to fit the selected location syntactically. In another example, if a selected fact specifies a family history of a certain condition, the gender of one or more pronouns within the generated text may be adjusted based on whether the user selects a location in a sentence about a female relative or about a male relative. As in other situations, if the user selecting an option from a structured choice and/or specifying a location in the text narrative is a person other than clinician 120, in some embodiments clinician 120 may be prompted to approve the user's selections prior to finally approving the set of clinical facts.

Figure 6:
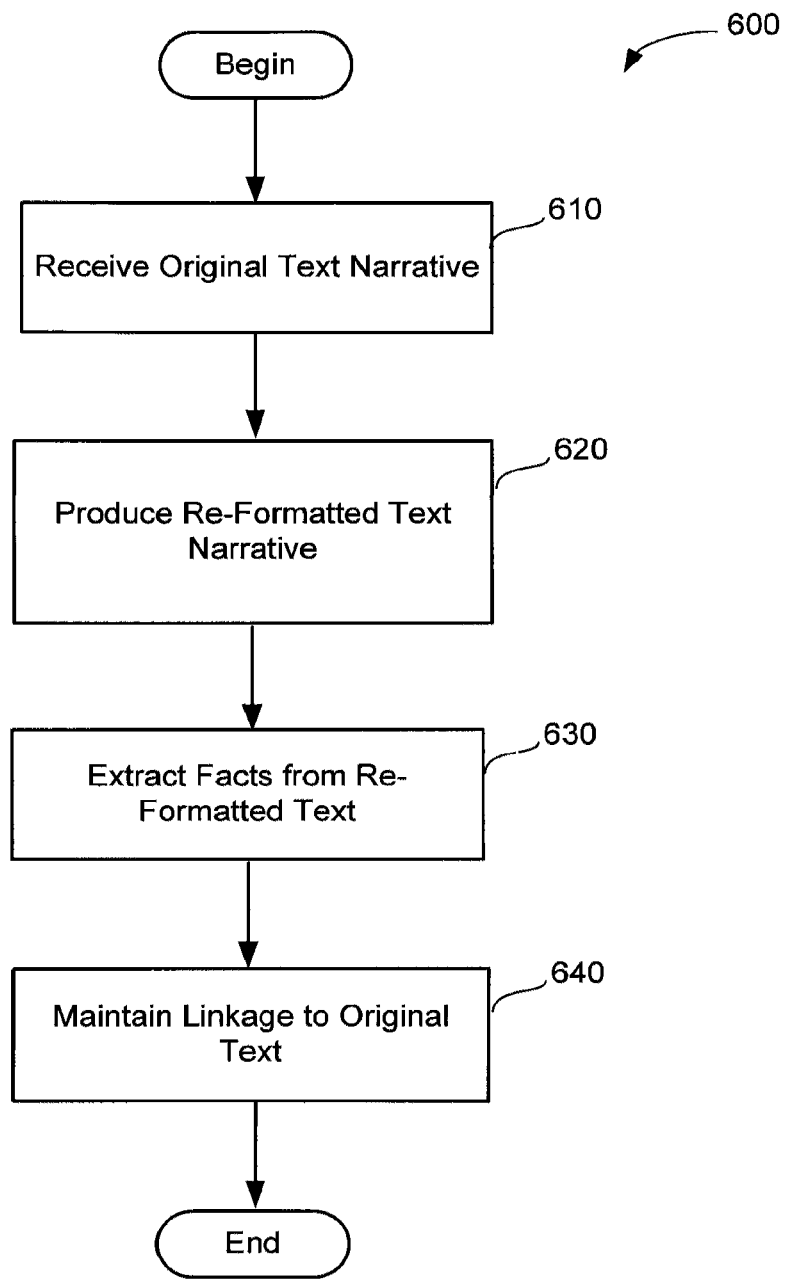
FIG. 6 is a flowchart illustrating an exemplary method for formatting text for clinical fact extraction in accordance with some embodiments of the present invention.

It should be appreciated from the foregoing that one embodiment of the invention is directed to a method 600 for formatting text for clinical fact extraction, as illustrated in FIG. 6. Method 600 may be performed, for example, by one or more components of a fact review system such as ASR engine 102 and/or CLU engine 104, although other implementations are possible and method 600 is not limited in this respect. Method 600 begins at act 610, at which an original text narrative (e.g., a textual representation of a narration of a patient encounter provided by a clinician) may be received. At act 620, the original text may be re-formatted to produce a formatted text narrative. At act 630, one or more clinical facts may be extracted from the formatted text. Method 600 ends at act 640, at which a linkage between at least one of the clinical facts and a corresponding portion of the original text may be maintained.

Figure 7:
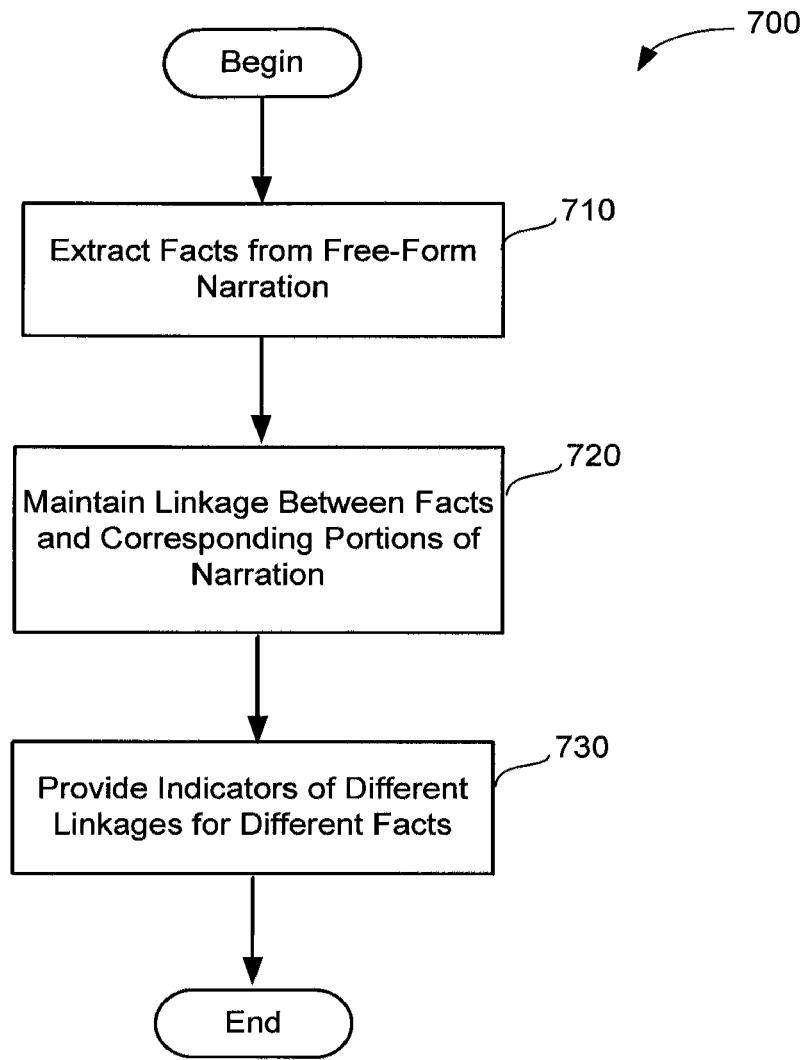
FIG. 7 is a flowchart illustrating an exemplary method for linking extracted clinical facts to text in accordance with some embodiments of the present invention.

It should be appreciated from the foregoing that another embodiment of the invention is directed to a method 700 for linking extracted clinical facts to text, as illustrated in FIG. 7. Method 700 may be performed, for example, by one or more components of a fact review system such as CLU engine 104 and/or fact review component 106, although other implementations are possible and method 700 is not limited in this respect. Method 700 begins at act 710, at which a plurality of facts may be extracted from a free-form narration of a patient encounter provided by a clinician. At act 720, a linkage may be maintained between each fact (or at least two of the facts) and the corresponding portion of the free-form narration from which it was extracted. Method 700 ends at act 730, at which a different indicator may be provided for each fact, to indicate the linkage between that fact and its corresponding portion of the free-form narration.

Figure 8:
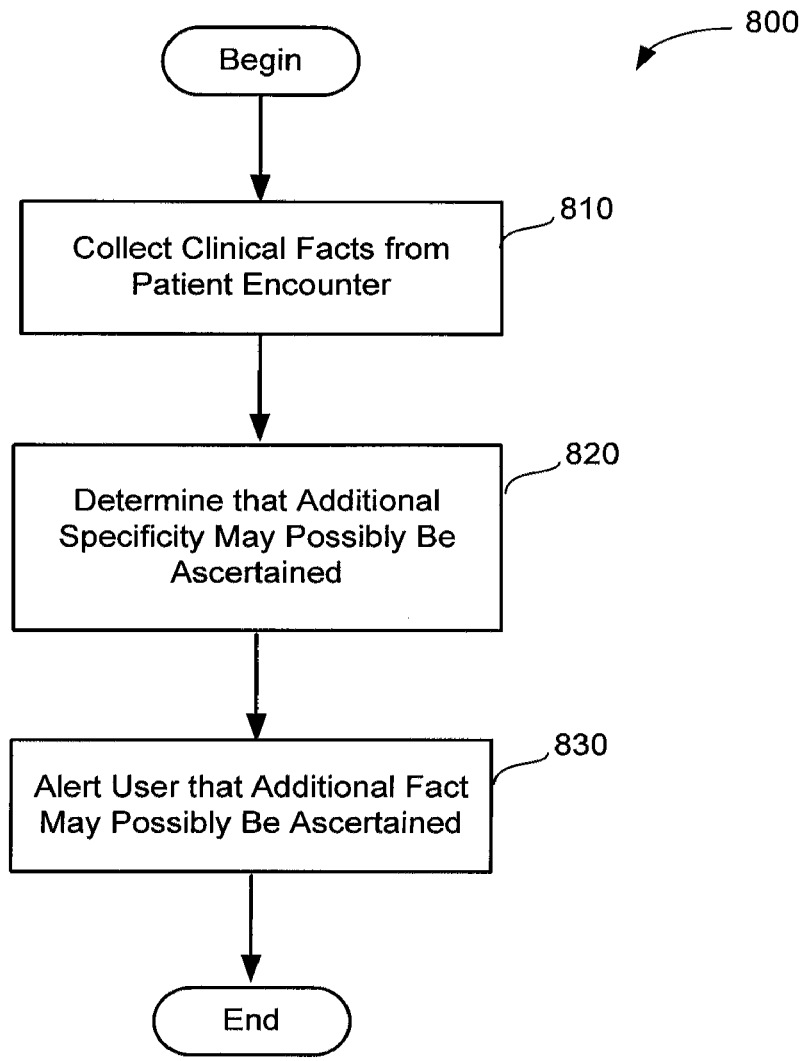
FIG. 8 is a flowchart illustrating an exemplary method for analyzing specificity in accordance with some embodiments of the present invention.

It should be appreciated from the foregoing that another embodiment of the invention is directed to a method 800 for analyzing specificity in clinical documentation, as illustrated in FIG. 8. Method 800 may be performed, for example, by one or more components of a fact review system such as ASR engine 102, CLU engine 104 and/or fact review component 106, although other implementations are possible and method 800 is not limited in this respect. Method 800 begins at act 810, at which a set of one or more clinical facts may be collected from a clinician's encounter with a patient. At act 820, it may be determined from the set of facts that additional specificity may possibly be ascertained from the patient encounter. Method 800 ends at act 830, at which a user may be alerted that an additional fact adding specificity to the set of facts may possibly be ascertained from the patient encounter.

Figure 9:
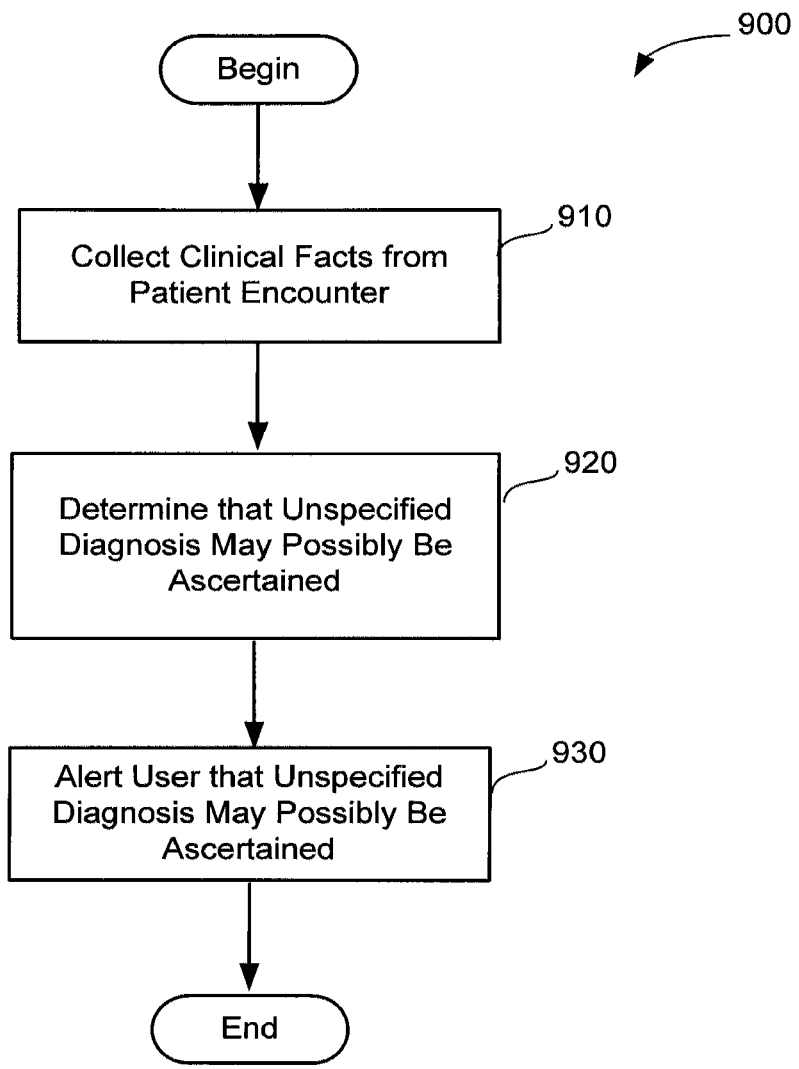
FIG. 9 is a flowchart illustrating an exemplary method for identifying an unspecified diagnosis in accordance with some embodiments of the present invention.

It should be appreciated from the foregoing that another embodiment of the invention is directed to a method 900 for identifying unspecified diagnoses in clinical documentation, as illustrated in FIG. 9. Method 900 may be performed, for example, by one or more components of a fact review system such as ASR engine 102, CLU engine 104 and/or fact review component 106, although other implementations are possible and method 900 is not limited in this respect. Method 900 begins at act 910, at which a set of one or more clinical facts may be collected from a clinician's encounter with a patient. At act 920, it may be determined from the set of facts that an unspecified diagnosis may possibly be ascertained from the patient encounter. Method 900 ends at act 930, at which a user may be alerted that the unspecified diagnosis may possibly be ascertained from the patient encounter.

Figure 10:
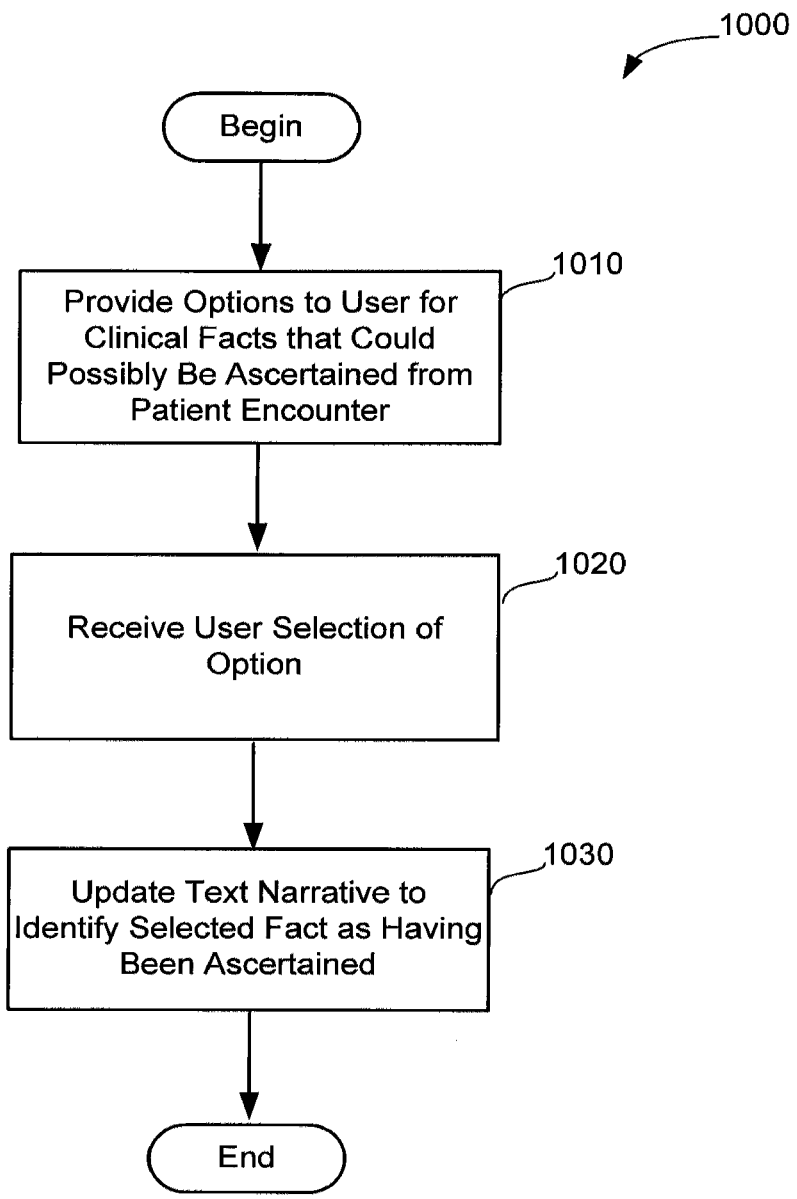
FIG. 10 is a flowchart illustrating an exemplary method for updating text in accordance with some embodiments of the present invention.

It should be appreciated from the foregoing that another embodiment of the invention is directed to a method 1000 for updating text in clinical documentation, as illustrated in FIG. 10. Method 1000 may be performed, for example, by one or more components of a fact review system such as CLU engine 104 and/or fact review component 106, although other implementations are possible and method 1000 is not limited in this respect. Method 1000 begins at act 1010, at which one or more options may be provided to a user, the one or more options corresponding to one or more clinical facts that could possibly be ascertained from a patient encounter. At act 1020, a user selection of one of the options may be received. Method 1000 ends at act 1030, at which a text narrative (e.g., a textual representation of a free-form narration of the patient encounter provided by a clinician) may be updated to identify the fact corresponding to the selected option as having been ascertained from the patient encounter.

Figure 11:
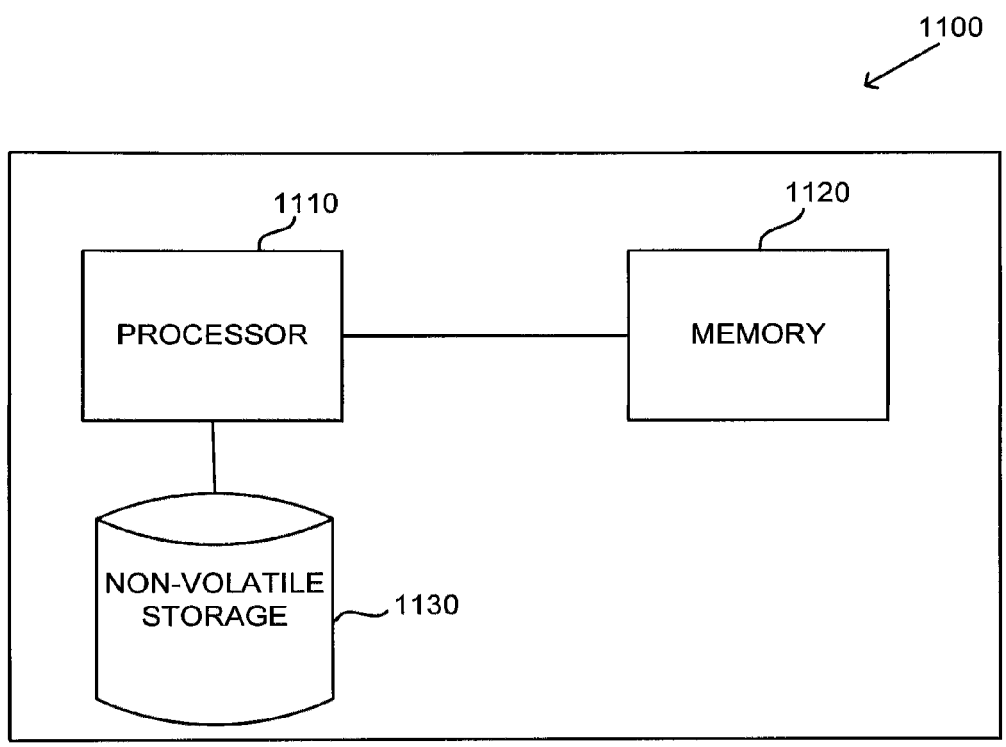
FIG. 11 is a block diagram of an exemplary computer system on which aspects of the present invention may be implemented.

A clinical fact review system in accordance with the techniques described herein may take any suitable form, as aspects of the present invention are not limited in this respect. An illustrative implementation of a computer system 1100 that may be used in connection with some embodiments of the present invention is shown in FIG. 11. One or more computer systems such as computer system 1100 may be used to implement any of the functionality described above. The computer system 1100 may include one or more processors 1110 and one or more tangible, non-transitory computer-readable storage media (e.g., memory 1120 and one or more non-volatile storage media 1130, which may be formed of any suitable non-volatile data storage media). The processor 1110 may control writing data to and reading data from the memory 1120 and the non-volatile storage device 1130 in any suitable manner, as the aspects of the present invention described herein are not limited in this respect. To perform any of the functionality described herein, the processor 1110 may execute one or more instructions stored in one or more computer-readable storage media (e.g., the memory 1120), which may serve as tangible, non-transitory computer-readable storage media storing instructions for execution by the processor 1110.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of embodiments of the present invention comprises at least one computer-readable storage medium (e.g., a computer memory, a floppy disk, a compact disk, a magnetic tape, or other tangible, non-transitory computer-readable medium) encoded with a computer program (i.e., a plurality of instructions), which, when executed on one or more processors, performs the above-discussed functions of one or more embodiments of the present invention. The computer-readable storage medium can be transportable such that the program stored thereon can be loaded onto any computer resource to implement aspects of the present invention discussed herein. In addition, it should be appreciated that the reference to a computer program which, when executed, performs any of the above-discussed functions, is not limited to an application program running on a host computer. Rather, the term computer program is used herein in a generic sense to reference any type of computer code (e.g., software or microcode) that can be employed to program one or more processors to implement above-discussed aspects of the present invention.

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A method comprising:
  accessing a free-form text documenting a patient encounter;
  analyzing the free-form text, using at least one processor, to extract a first set of one or more medical facts from a first portion of the free-form text, the analyzing comprising
    processing the free-form text to identify a set of one or more features of the first portion of the free-form text,
    correlating the set of features to one or more abstract semantic concepts, and
    generating computer-readable data that expresses the one or more abstract semantic concepts as the one or more medical facts extracted from the first portion of the free-form text;
  receiving, from a user documenting the patient encounter, a correction to the first set of medical facts extracted from the first portion of the free-form text; and
  applying the user's correction in extracting a second set of one or more medical facts from a second portion of the free-form text.

2. The method of claim 1, wherein the user's correction comprises removing a fact from the first set of facts, and wherein applying the user's correction in extracting the second set of facts comprises suppressing extraction of one or more facts similar to the removed fact from the second portion of the free-form text.

3. The method of claim 1, wherein the user's correction comprises adding a fact to the first set of facts, and wherein applying the user's correction in extracting the second set of facts comprises extracting one or more facts similar to the identified fact from the second portion of the free-form text.

4. Apparatus comprising:
  at least one processor; and
  at least one computer-readable storage medium storing processor-executable instructions that, when executed by the at least one processor, perform a method comprising:
    accessing a free-form text documenting a patient encounter;
    analyzing the free-form text to extract a first set of one or more medical facts from a first portion of the free-form text, the analyzing comprising
      processing the free-form text to identify a set of one or more features of the first portion of the free-form text,
      correlating the set of features to one or more abstract semantic concepts, and
      generating computer-readable data that expresses the one or more abstract semantic concepts as the one or more medical facts extracted from the first portion of the free-form text;
    receiving, from a user documenting the patient encounter, a correction to the first set of medical facts extracted from the first portion of the free-form text; and
    applying the user's correction in extracting a second set of one or more medical facts from a second portion of the free-form text.

5. The apparatus of claim 4, wherein the user's correction comprises removing a fact from the first set of facts, and wherein applying the user's correction in extracting the second set of facts comprises suppressing extraction of one or more facts similar to the removed fact from the second portion of the free-form text.

6. The apparatus of claim 4, wherein the user's correction comprises adding a fact to the first set of facts, and wherein applying the user's correction in extracting the second set of facts comprises extracting one or more facts similar to the identified fact from the second portion of the free-form text, narrative.

7. At least one non-transitory computer-readable storage medium encoded with computer-executable instructions that, when executed, perform a method comprising:
   accessing a free-form text documenting a patient encounter;
   analyzing the free-form text to extract a first set of one or more medical facts from a first portion of the free-form text, the analyzing comprising
      processing the free-form text to identify a set of one or more features of the first portion of the free-form text,
      correlating the set of features to one or more abstract semantic concepts, and
      generating computer-readable data that expresses the one or more abstract semantic concepts as the one or more medical facts extracted from the first portion of the free-form text;
   receiving, from a user documenting the patient encounter, a correction to the first set of medical facts extracted from the first portion of the free-form text; and
   applying the user's correction in extracting a second set of one or more medical facts from a second portion of the free-form text.

8. The at least one non-transitory computer-readable storage medium of claim 7, wherein the user's correction comprises removing a fact from the first set of facts, and wherein applying the user's correction in extracting the second set of facts comprises suppressing extraction of one or more facts similar to the removed fact from the second portion of the free-form text.

9. The at least one non-transitory computer-readable storage medium of claim 7, wherein the user's correction comprises adding a fact to the first set of facts, and wherein applying the user's correction in extracting the second set of facts comprises extracting one or more facts similar to the identified fact from the second portion of the free-form text.

* * * * *